United States Patent
Schecter

(10) Patent No.: US 8,328,728 B2
(45) Date of Patent: Dec. 11, 2012

(54) IMPLANTABLE HEMODYNAMIC MONITOR AND METHODS FOR USE THEREWITH

(75) Inventor: Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 1142 days.

(21) Appl. No.: 12/196,632

(22) Filed: Aug. 22, 2008

(65) Prior Publication Data

US 2010/0049060 A1  Feb. 25, 2010

(51) Int. Cl.
*A61B 5/02* (2006.01)
*A61B 5/04* (2006.01)

(52) U.S. Cl. ........ 600/486; 600/481; 600/485; 600/493; 600/500; 600/501; 600/505; 600/509; 600/513; 600/514; 600/526; 607/6; 607/17; 607/18; 607/23

(58) Field of Classification Search .......... 600/481, 600/485, 486, 490, 508, 493, 500, 501, 505, 600/509, 513, 514, 526; 607/6, 17, 18, 23
See application file for complete search history.

(56) References Cited

U.S. PATENT DOCUMENTS

| | | | |
|---|---|---|---|
| 4,406,289 A * | 9/1983 | Wesseling et al. | 600/483 |
| 4,418,700 A | 12/1983 | Warner | |
| 4,475,554 A | 10/1984 | Hyndman | |
| 4,562,843 A | 1/1986 | Djordjevich et al. | |
| 4,686,988 A | 8/1987 | Sholder | |
| 4,708,142 A | 11/1987 | DeCote, Jr. | |
| 4,712,555 A | 12/1987 | Thornander et al. | |
| 4,729,376 A | 3/1988 | Decote, Jr. | |
| 4,731,051 A | 3/1988 | Fischell | |
| 4,788,980 A | 12/1988 | Mann et al. | |
| 4,809,697 A | 3/1989 | Causey, III et al. | |
| 4,834,107 A | 5/1989 | Warner | |
| 4,940,052 A | 7/1990 | Mann et al. | |
| 4,944,298 A | 7/1990 | Sholder | |
| 4,944,299 A | 7/1990 | Silvian | |
| 4,947,845 A | 8/1990 | Davis | |
| 4,969,467 A | 11/1990 | Callaghan et al. | |
| 5,111,817 A | 5/1992 | Clark et al. | |
| 5,265,615 A | 11/1993 | Frank et al. | |
| 5,350,410 A | 9/1994 | Kleks et al. | |

(Continued)

FOREIGN PATENT DOCUMENTS

WO  9111137  8/1991

(Continued)

OTHER PUBLICATIONS

Buclin, T. et al. Evaluation of noninvasive blood pressure recording by photoplethysmography in clinical studies using angiotensin challenges. Clin Pharmacol. 48: 586-593 (1999)).*

(Continued)

*Primary Examiner* — Gail R Gabel

(57) ABSTRACT

Provided herein are implantable systems that include an implantable photoplethysmography (PPG) sensor, which can be used to obtain an arterial PPG waveform. In an embodiment, a metric of a terminal portion of an arterial PPG waveform is determined, and a metric of an initial portion of the arterial PPG waveform is determined, and a surrogate of mean arterial pressure is determined based on the metric of the terminal portion and the metric of the initial portion. In another embodiment, a surrogate of diastolic pressure is determined based on a metric of a terminal portion of an arterial PPG waveform. In a further embodiment, a surrogate of cardiac afterload is determined based on a metric of a terminal portion of an arterial PPG waveform.

4 Claims, 15 Drawing Sheets

U.S. PATENT DOCUMENTS

| | | | |
|---|---|---|---|
| 5,533,511 | A | 7/1996 | Kaspari et al. |
| 5,540,727 | A | 7/1996 | Tockman et al. |
| 5,766,127 | A | 6/1998 | Pologe et al. |
| 5,862,805 | A | 1/1999 | Nitzan |
| 5,865,755 | A | 2/1999 | Golub |
| 6,112,116 | A | 8/2000 | Fischell et al. |
| 6,120,459 | A | 9/2000 | Nitzan et al. |
| 6,272,379 | B1 | 8/2001 | Fischell et al. |
| 6,275,734 | B1 | 8/2001 | McClure et al. |
| 6,280,390 | B1 | 8/2001 | Akselrod et al. |
| 6,409,675 | B1 | 6/2002 | Turcott |
| 6,466,821 | B1 | 10/2002 | Pianca et al. |
| 6,491,639 | B1 | 12/2002 | Turcott |
| 6,561,984 | B1 | 5/2003 | Turcott |
| 6,575,912 | B1 | 6/2003 | Turcott |
| 6,609,023 | B1 | 8/2003 | Fischell et al. |
| 6,616,613 | B1 | 9/2003 | Goodman |
| 6,625,493 | B2 | 9/2003 | Kroll et al. |
| 6,658,292 | B2 | 12/2003 | Kroll et al. |
| 6,731,967 | B1 | 5/2004 | Turcott |
| 6,792,310 | B1 | 9/2004 | Turcott et al. |
| 6,887,207 | B2 * | 5/2005 | Hettrick .................. 600/485 |
| 7,177,686 | B1 | 2/2007 | Turcott |
| 7,212,861 | B1 | 5/2007 | Park et al |
| 7,302,294 | B2 | 11/2007 | Kamath et al. |
| 7,403,813 | B1 | 7/2008 | Farazi et al. |
| 2006/0074322 | A1 | 4/2006 | Nitzan |
| 2007/0191901 | A1 | 8/2007 | Schecter |
| 2009/0131804 | A1 * | 5/2009 | Mukkamala et al. ......... 600/485 |

FOREIGN PATENT DOCUMENTS

| | | |
|---|---|---|
| WO | 9518564 | 7/1995 |
| WO | 0204094 A1 | 1/2002 |

OTHER PUBLICATIONS

Buclin, T. et al., "Evaluation of noninvasive blood pressure recording by photoplethysmography in clinical studies using angiotensin challenges," Clin Pharmacol. 1999;48:586-593.

Kelly, Raymond et al., "Effective Arterial Elastance as Index of Arterial Vascular Load in Humans," Circulation. 1992;86:513-521.

Natalini, Giuseppe MD et al., "Variations in Arterial Blood Pressure and Photoplethysmography During Mechanical Ventilation," Technology, Computing, and Stimulation. 2006;103(5):1182-1188.

O'Rourke, M., "Coupling between the left ventricle and arterial system in hypertension," European Heart Journal. 1990;11(Supplement):24-28.

Starling, Mark R. MD, "Left ventricular-arterial coupling relations in the normal human heart," Am Heart J. 1993;125:1659-1666.

Wesseling, K.H. et al., "Computation of aortic flow from pressure in humans using a nonlinear, three-element model," J Appl Physiol. 1993;74(5):2566-2573.

Malkoff, White Paper, "Non-Invasive Blood Pressure for Mice and Rats," http://kentscientific.com/images/customer-files/NIBP_White_Paper.pdf.

* cited by examiner

IMPLANTABLE HEMODYNAMIC MONITOR AND METHODS FOR USE THEREWITH

FIELD OF THE INVENTION

Embodiments of the present invention relate to implantable systems for monitoring various hemodynamic metrics, and methods for use therewith.

BACKGROUND OF THE INVENTION

A person's circulatory system includes both systemic and pulmonary circulation systems. Pulmonary circulation supplies the lungs with blood flow, while the systemic circulation takes care of all the other parts of the body, i.e. the systemic circulation. The heart serves as a pump that keeps up the circulation of the blood. Both the pulmonary and systemic circulatory systems are made up of arteries, arterioles, capillaries, venules and veins. The arteries take the blood from the heart, while the veins return the blood to the heart Blood pressure is defined as the force exerted by the blood against any unit area of the vessel wall. The measurement unit of blood pressure is millimeters of mercury (mmHg). Pulmonary and systemic arterial pressures are pulsatile, having systolic and diastolic pressure values. The highest recorded pressure reading is called systolic pressure, which results from the active contraction of the ventricle. Although the arterial pressure and indeed flow in the arteries is pulsatile, the total volume of blood in the circulation remains constant. The lowest pressure reading is called diastolic pressure which is maintained by the resistance created by the smaller blood vessels still on the arterial side of the circulatory system (arterioles). Stated another way, the systolic pressure is defined as the peak pressure in the arteries, which occurs near the beginning of a cardiac cycle. In contrast, the diastolic pressure is the lowest pressure, which occurs at the resting phase of the cardiac cycle. The pulse pressure reflects the difference between the maximum and minimum pressures measured (i.e., the difference between the systolic pressure and diastolic pressure). The mean arterial pressure is the average pressure throughout the cardiac cycle.

Arterial pulse pressure, such as mean arterial pressure (MAP), is a fundamental clinical parameter used in the assessment of hemodynamic status of a patient. Mean arterial pressure can be estimated from real pressure data in a variety of ways. Among the techniques that have been proposed, two are presented below. In these formulas, SP is the systolic blood pressure, and DP is diastolic pressure.

a. $MAP_2 = (SP + 2DP)/3 = \frac{1}{3}(SP) + \frac{2}{3}(DP)$ b. $MAP_1 = (SP + DP)/2$ Systolic pressure and diastolic pressure can be obtained in a number of ways. A common approach is to use a stethoscope, an occlusive cuff, and a pressure manometer. However, such an approach is slow, requires the intervention of a skilled clinician and does not provide timely readings as it is a measurement at only a single point in time. While systolic pressure and diastolic pressure can also be obtained in more automated fashions, it is not always practical to obtain measures of pressure using a cuff and pressure transducer combination, especially if the intention or desire is to implant a sensor that can monitor arterial pressure on a chronic basis.

Another approach for obtaining measures of arterial pressure is to use an intravascular pressure transducer. However, an intravascular device may cause problems, such as, embolization, nerve damage, infection, bleeding and/or vessel wall damage. Additionally, the implantation of an intravascular lead requires a highly skilled physician such as a surgeon, electrophysiologist, or interventional cardiologist.

Plethysmography, the measurement of volume of an organ or body part, has a history that extends over 100 years. Photoplethysmography (PPG) uses optical techniques to perform volume measurements, and was first described in the 1930s. While best known for their role in pulse oximetry, PPG sensors have also been used to indirectly measure blood pressure. For example, non-invasive PPG sensors have been used in combination with in an inflatable cuff in a device known as Finapres. U.S. Pat. No. 4,406,289 (Wesseling et al.) and U.S. Pat. No. 4,475,940 (Hyndman) are exemplary patents that relate to the Finapres technique. The cuff is applied to a patient's finger, and the PPG sensor measures the absorption at a wavelength specific for hemoglobin. After the cuff is used to measure the individual's mean arterial pressure, the cuff pressure around the finger is then varied to maintain the transmural pressure at zero as determined by the PPG sensor. The Finapres device tracks the intra-arterial pressure wave by adjusting the cuff pressure to maintain the optical absorption constant at all times.

There are a number of disadvantages to the Finapres technique. For example, when there exists peripheral vasoconstriction, poor vascular circulation, or other factors, the blood pressure measured in a finger is not necessarily representative of central blood pressure. Further, maintaining continuous cuff pressure causes restriction of the circulation in the finger being used, which is uncomfortable when maintained for extended periods of time. Accordingly, the Finapres technique is not practical for chronic use. Additionally, because of the need for a pneumatic cuff, a Finapres device can not be used as an implanted sensor.

Simple external blood pressure monitors also exist, but they do not offer continuous measurement and data logging capability. These devices can be purchased at a drug store, but patient compliance is required to make regular measurements and accurately record the data. Additionally, portable external miniature monitors that automatically log blood pressure data exist, but these devices can only store a day or so of data and require clinician interaction to download and process the measured data.

As is evident from the above description, there is the need for improved systems and methods for monitoring arterial blood pressure, including systolic pressure, diastolic pressure and mean arterial pressure.

Ventricular afterload, also known as cardiac afterload (CA), may be defined as the mechanical force opposing ventricular ejection, as for example described by W. R. Milnor, "Arterial Impedance as Ventricular Load," Circulation Research, 1975;36:565-70. This mechanical opposition of the flow of the viscous blood through the visco-elastic arterial system has two major mechanical components determined by the mechanical properties of the arterial system including hydraulic resistance and arterial compliance.

Hydraulic resistance is a function of several factors including the smooth muscle tone of the arterial system that determines arterial dimension, the dimensions and patency of the aortic or pulmonic valve, the geometry of the ventricular outflow tract, thickness of the ventricular myocardium, the length of the arterial vessels and the viscosity of the blood. Hydraulic resistance is proportional to ventricular afterload and can be described in general by Poisuelle's law or by Ohm's law, which states that systemic vascular resistance (also referred to as total peripheral resistance) is equal to the difference between mean arterial pressure and central venous pressure divided by cardiac output. Hydraulic resistance is typically estimated clinically by invasive or non-invasive estimates of mean arterial pressure and cardiac output.

Arterial compliance describes the ability of the arterial blood vessels to store a portion of the energy delivered to the arterial system by the ventricles during systole and return that energy to the arterial blood during ventricular diastole in order to maintain diastolic arterial blood pressure and flow. Arterial compliance is inversely proportional to ventricular afterload. Clinical estimates of arterial compliance are difficult to measure. It is occasionally approximated by aortic distensibility, or the change in aortic pressure divided by the change in aortic cross-sectional area. Another estimate of arterial compliance is "effective arterial elastance" as described, for example, by R. P Kelly et al., in "Effective Arterial Elastance as an Index of Arterial Vascular Load in Humans," Circulation 1992;86:513-521. Estimation of this parameter requires measurement of ventricular pressure and volume.

Ventricular afterload includes both arterial resistance and arterial compliance, and may also be estimated using lumped or distributed mathematical models such as for example the three-element Windkessel model described by K. H. Wesseling et al., "Computation of Aortic Flow from Pressure in Humans Using a Non-linear, Three-element Model," J. Appl. Physiol., 1993;74:425-35. The mathematical solution to these models requires measurement of both aortic blood pressure and flow.

The term "ventricular arterial coupling" describes the mechanical relationship between the ventricles and the arterial system during ventricular ejection as described for example by M. R. Starling, "Left Ventricular-arterial Coupling Relations in the Normal Human Heart," Am. Heart J., 1993;125:1659-66. Cardiovascular function may be maintained even if ventricular contractile function is reduced by a compensatory decrease in ventricular afterload (either by decreased resistance, increased compliance or both). For example, administration of nitroglycerin during an episode of myocardial ischemia can maintain cardiac output despite decreased ventricular contractility by reducing arterial tone, increasing arterial compliance and hence decreasing ventricular afterload. Measurement of ventricular arterial coupling parameters involves measurement of both ventricular pressure and volume.

Regional or global changes in ventricular afterload including arterial resistance and compliance may alter patterns of arterial wave reflection. These changes in arterial wave reflection patterns may be manifest by changes in pressure signals measured in the arteries or ventricles as demonstrated for example by M. O'Rourke, "Coupling Between the Left Ventricle and Arterial System in Hypertension," Eur. Heart J. 1990;11(G):24-28. Thus, changes in the morphometry of ventricular or arterial blood pressure signals can indicate changes in the resistive and compliant properties of the arterial system and hence can indicate changes in ventricular afterload.

The core of the altered cardiovascular function in HF is a depression of cardiac contractility. Therefore, an adequate assessment of cardiovascular function, including right or left ventricular afterload, has important diagnostic and therapeutic implications. Patients with acute HF, particularly as a complication of acute myocardial infarction or as an acute exacerbation of a previously compensated chronic HF, have a high mortality rate of about 30% within the first 12 months. In this clinical condition, a proper evaluation of ventricular afterload is extremely important for diagnostic purposes to assess the severity of the process and as a guide for the inotropic, vasodilator, or diuretic therapy. Typically, resistance indices are used to evaluate ventricular afterload, such as systolic arterial blood pressure, systemic vascular resistance or peak ventricular wall stress, with the serious limitations that these parameters have, since they ignore arterial compliance. Ventricular afterload may be estimated using aortic (or pulmonary) input impedance. However, this index requires the measurement of both pressure and flow and is difficult to interpret clinically.

Multiple clinical pathologies may result in acute or chronic changes in ventricular afterload including valvular disease, hypertension, ventricular hypertrophy, hypertrophic cardiomyopathy, atherosclerotic plaque formation, arterial thrombus, systemic shock, etc. In addition any vasoactive substance that affects arterial or venous tone, such as but not limited to nitro-glycerin, sodium nitro-prusside, neosynephrine, or epinephrine, can dramatically alter ventricular afterload. Hence, the ability to monitor ventricular afterload is extremely desirable. Further, it would be desirable if such ability was provided to a chronically implantable cardiac device.

An implantable system for measuring ventricular afterload has been proposed in U.S. Pat. No. 6,887,207. However, the proposed implantable system includes a pressure sensor implanted with the right ventricle near the outflow tract of a patient's heart. Accordingly, the proposed system relies on invasive intracardiac sensors. Such an intracardiac sensor may cause problems, such as, embolization, nerve damage, infection, bleeding and/or cardiac or vessel wall damage. Additionally, the implantation of an intracardiac sensor requires a highly skilled physician such as a surgeon, electrophysiologist, or interventional cardiologist. Accordingly, there is still a need for improved systems and methods for monitoring ventricular afterload.

SUMMARY OF THE INVENTION

Embodiments of the present invention relate to implantable systems, and methods for use therewith. Specific embodiments of the present invention relate to implantable systems that include an implantable photoplethysmography (PPG) sensor, and methods for use therewith.

Certain embodiments of the present invention relate to monitoring mean arterial pressure (MAP) based on an arterial PPG waveform obtained using an implantable PPG sensor. An arterial PPG waveform is obtained using the implantable PPG sensor. A metric of a terminal portion (Tmetric) of the arterial photoplethysmography (PPG) waveform is determined, wherein the terminal portion is from a maximum of the arterial PPG waveform to a following minimum of the PPG waveform. Additionally, a metric of an initial portion (Imetric) of the arterial PPG waveform is determined, wherein the initial portion is from a minimum of the arterial PPG waveform to the following maximum of the PPG waveform. Based on the metric of the terminal portion and the metric of the initial portion, a surrogate of MAP is determined. In accordance with an embodiment, the above is repeated from time to time, and changes in MAP are monitored by monitoring changes in the surrogate of MAP as the above is repeated from time to time. In accordance with an embodiment, the arterial PPG waveform is an averaged arterial PPG waveform that is produced by averaging a plurality of cardiac cycles of a PPG signal obtained from an implanted extravascular PPG sensor.

In an embodiment, the Tmetric is an integral from a maximum to the following minimum of the arterial PPG waveform, and the Imetric is an integral from a minimum of the arterial PPG waveform to the following maximum of the PPG waveform. In an embodiment, the Tmetric is an integral from a dicrotic notch to the following minimum of the PPG waveform, and the Imetric is an integral from a minimum of the arterial PPG waveform to the following maximum of the PPG waveform. In an embodiment, the Tmetric is a terminal deceleration slope (TDS) or a beginning terminal deceleration slope (BTDS), where the TDS is a downward slope from a maximum to the following minimum of the arterial PPG waveform, and the BTDS is a downward slope from a maximum to the following dicrotic notch of the arterial PPG waveform, and the Imetric is an initial acceleration slope (IAS), which is an upward slope from a minimum to the following maximum of the arterial PPG waveform. In an embodiment, the Tmetric is a total relaxation time (TRT), which is a time from a maximum to the following minimum of the atrial PPG signal, and the Imetric is an initial acceleration time (IAT), which is a time from a minimum to the following maximum of the arterial PPG signal. In an embodiment, the Tmetric is a terminal deceleration time (TeDT), which is a time from a dicrotic notch to the following minimum of the atrial PPG signal, and the Imetric is an initial acceleration time (IAT), which is a time from a minimum to the following maximum of the arterial PPG signal.

Certain embodiments of the present invention relate to monitoring diastolic pressure (DP). An arterial PPG waveform is obtained using the implantable PPG sensor. A surrogate of DP is determined by determining a metric of a terminal portion of an arterial photoplethysmography (PPG) waveform, wherein the terminal portion is from a maximum of the arterial PPG waveform to the following minimum of the PPG waveform. The above is repeated from time to time, and changes in DP are monitored by monitoring changes in the surrogate of DP as the above is repeated from time to time. In an embodiment, the metric of the terminal portion includes at least one of the following: an integral from a maximum to the following minimum of the arterial PPG waveform; an integral from a dicrotic notch to the following minimum of the PPG waveform; a terminal deceleration slope (TDS), which is a downward slope from a maximum to the following minimum of the arterial PPG waveform; a beginning terminal deceleration slope (BTDS), which is a downward slope from a maximum to the following dicrotic notch of the arterial PPG waveform; a total relaxation time (TRT), which is a time from a maximum to the following minimum of the atrial PPG signal; and a terminal deceleration time (TeDT), which is a time from a dicrotic notch to the following minimum of the atrial PPG signal.

Other embodiments for monitoring DP include using implanted electrodes to obtain a first signal (e.g., an IEGM or ECG) indicative of electrical activity of the patient's heart, and using an implanted PPG sensor to obtain an arterial photoplethysmography (PPG) signal. A ventricular depolarization is detected in a portion of the first signal corresponding to a cardiac cycle. Additionally, one of a dicrotic notch and a minimum is detected in a portion of the arterial PPG signal corresponding to the same cardiac cycle. A time is determined from the detected ventricular depolarization to the detected one of the dicrotic notch and minimum in the arterial PPG signal. A surrogate of DP is determined based on the determined time. In accordance with an embodiment, the above is repeated from time to time, and changes in DP are monitored by monitoring changes in the surrogate of DP as the above is repeated from time to time.

Certain embodiments of the present invention relate to monitoring cardiac afterload (CA). Such embodiments include obtaining an arterial PPG waveform using an implantable PPG sensor. Additionally, a surrogate of CA is determined by determining a metric of a terminal portion of the arterial photoplethysmography (PPG) waveform, wherein the terminal portion is from a maximum of the arterial PPG waveform to the following minimum of the PPG waveform. Exemplary metrics of the terminal portion of an arterial PPG waveform were provided above. In accordance with an embodiment, the above is repeated from time to time, and changes in CA are monitored by monitoring changes in the surrogate of CA as the above is repeated from time to time.

Other features and advantages of the invention will appear from the following description in which the preferred embodiments have been set forth in detail, in conjunction with the accompanying drawings and claims.

DETAILED DESCRIPTION OF THE INVENTION

Figure 1A:
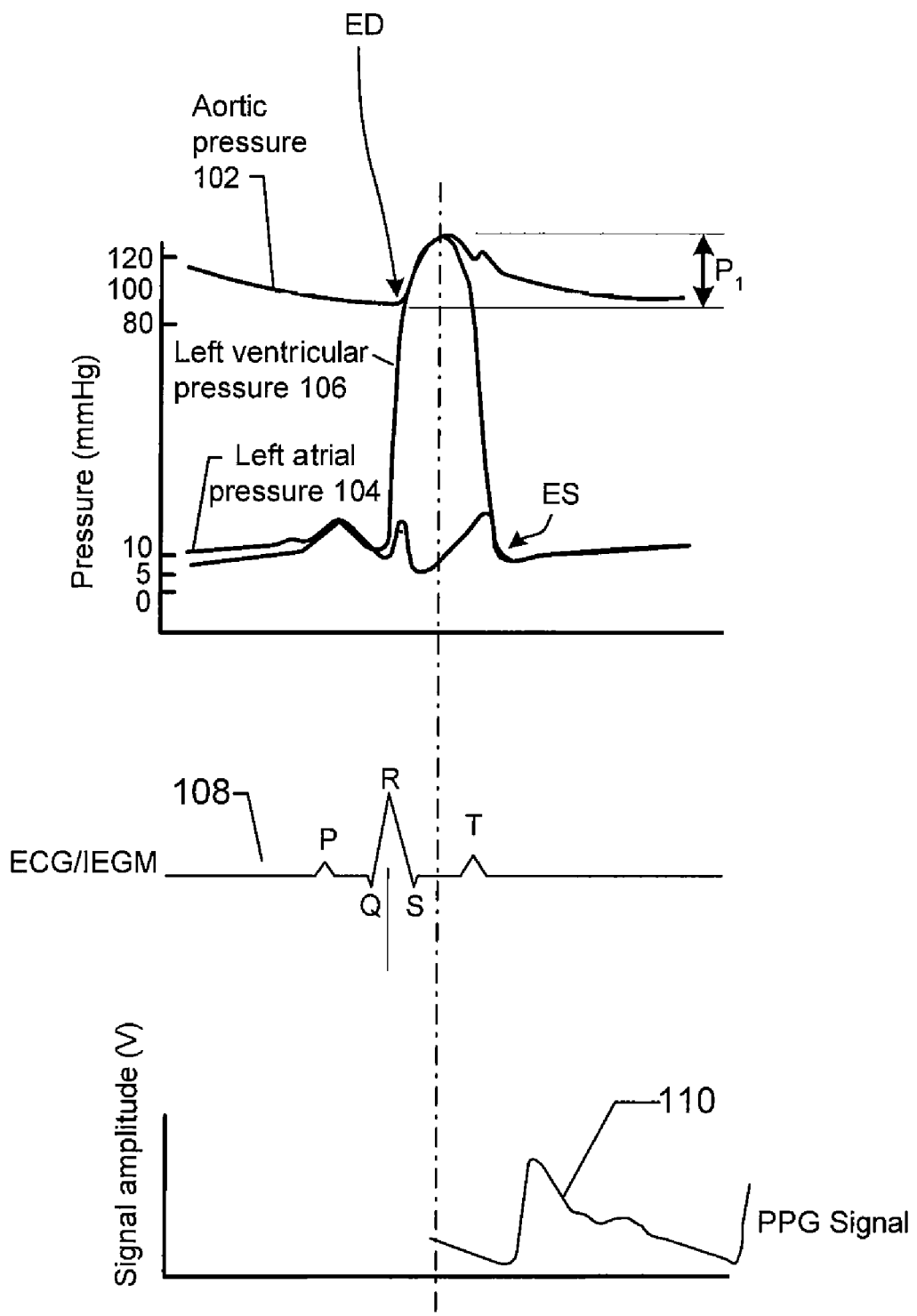
FIG. 1A includes signal waveforms that are used to show the relative timing of electrical and mechanical cardiac events that occur during a cardiac cycle. The upper graph includes an aortic pressure waveform, a left atrial pressure waveform and a left ventricular pressure waveform. The middle graph includes a signal indicative of electrical cardiac activity. The lower graph includes a photoplethysmography (PPG) signal, which is indicative of mechanical cardiac activity.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

Referring to FIG. 1, the exemplary signal waveforms therein are used to show the relative timing of electrical and mechanical cardiac events that occur during a cardiac cycle. The upper graph includes an exemplary aortic pressure waveform 102, an exemplary left atrial pressure waveform 104 and an exemplary left ventricular pressure waveform 106. The middle graph includes an exemplary electrocardiogram (ECG) or intracardiac electrogram (IEGM) waveform 108, which is shown as including a P wave, a QRS complex (including Q, R and S waves) and a T wave. The P wave is caused by depolarization of the atria. This is followed by atrial contraction, which is indicated by a slight rise in the atrial pressure (seen in waveform 104) contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T wave and this is associated with the onset of ventricular relaxation in which forward flow stops, the pressure in the ventricle falls below that in the atria at which time the mitral and tricuspid valves open to begin to passively fill the ventricle during diastole. Also shown in FIG. 1, in the bottom graph, is an exemplary photoplethysmography (PPG) signal 110, which will be described in additional detail below. Addition details of the morphology of a PPG waveform are discussed below, with reference to FIG. 2.

PPG Waveform

Certain embodiments of the present rely primarily (or at least partially) on the morphology of a PPG waveform to monitor arterial blood pressure and/or cardiac afterload. Accordingly, some additional details of the morphology of an exemplary PPG waveform shall now be described with reference to FIG. 2.

An implanted sensor is used to obtain the PPG signal. An exemplary PPG sensor, also referred to as an implanted optical sensor, is discussed below with reference to FIG. 8A-8C and 9. The PPG sensor can be implanted, e.g., in the pectoral region of a patient. Thus, it is practical that the PPG sensor can be integrated with or attached to the housing of a pacemaker or ICD, as can be appreciated from FIGS. 8A-8C and 9 discussed below. Alternative locations for implantation of the PPG sensor include, but are not limited to, the patient's leg, arm or neck.

Volume changes in blood vessels occur in a pulsatile manner with each beat of the heart as blood flows in and out of a portion of the body. A PPG sensor produces waveform measurements that are similar to arterial pressure waveform measurements, because changes in arterial pressure correspond to relative changes in blood volume.

Figure 1B:
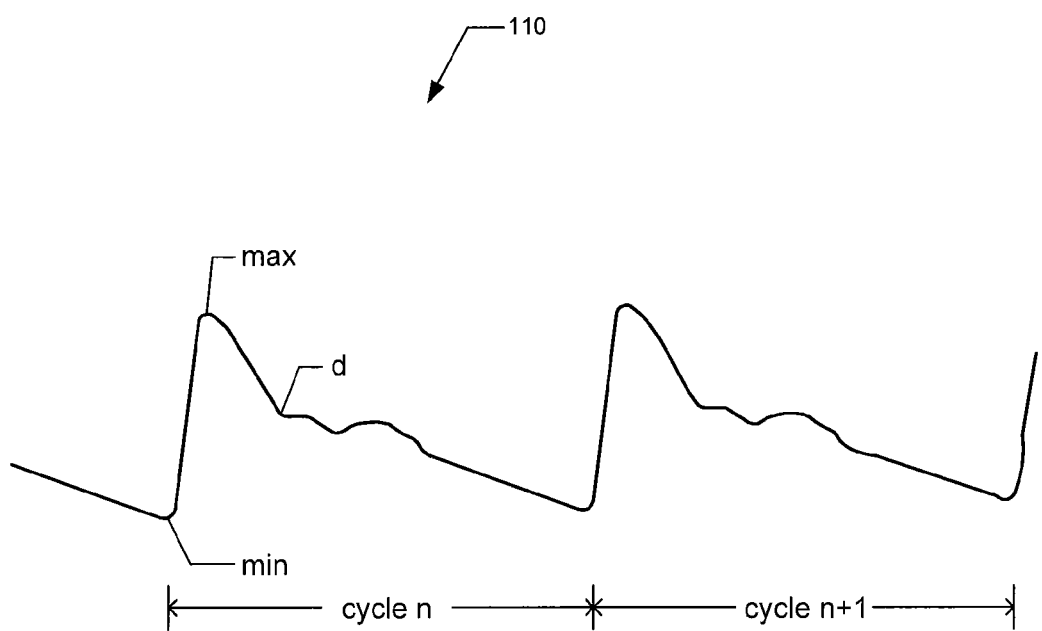
FIG. 1B shows two cycle of an exemplary PPG signal.

A portion of an exemplary PPG waveform 110, which can be obtained by an implanted extravascular PPG sensor, is shown in FIG. 1B. Each cycle of the PPG waveform 110 includes a minimum (min), a maximum (max), and a dicrotic notch (d) that follows the max. The portion of the PPG waveform from a min to following max shall also be referred to herein as the initial potion of the PPG waveform. The portion of the PPG waveform from a max to the following min shall be referred to as the terminal portion of the PPG waveform. The dicrotic notch (d), which is located in the terminal portion of the PPG waveform, is the first local minimum following a max in the PPG waveform.

The max (also referred to as peak) of the PPG signal 110 occurs at a time after the peak in the arterial blood pressure in the aorta at the level of the left ventricular outflow tract (note that this is representative of the time of peak pressure in the region illuminated by the PPG sensor). This is because the peak in the PPG signal 110 is indicative of the peak wave in arterial blood pressure generated by the patient's heart, as detected by a PPG sensor located a distance from the patient's heart. For example, if the PPG sensor is implanted in the pectoral region of the patient (which is an option, but not necessary), it can take a pulse wave (as detected from ECG/IEGM electrodes) on the order of 10-100 msec to travel from the patient's heart to the PPG sensor, depending on the location of the electrodes (used to obtain the ECG/IEGM) and the location of the PPG sensor.

Stated another way, a few tens to a few hundreds of milliseconds after the QRS complex, the PPG amplitude reaches a minimum and then starts to increase. This is due to the increasing blood volume in the arterioles as the systolic pulse reaches the periphery. The delay is influenced by the distance that the PPG sensor is placed from the heart. It requires approximately 100 msec for the amplitude of the waveform to reach its maximum. The excursion from minimum to maximum represents the arterial pulse amplitude. During diastole, the recoil of the elastic arterial vessels continues to force blood through the capillaries, so that blood flows through the capillary bed throughout the entire cardiac cycle.

Ventricular depolarization occurs at the beginning of systole, which substantially coincides with the end of diastole (ED in FIG. 1A). The maximum peak amplitude of the PPG signal 110 occurs when a mechanical pulse resulting from the ventricular depolarization is detected by the PPG sensor, which is a distance from a location in the patient's heart where the pulse originated. For example, the PPG sensor can be implanted in the pectoral region, e.g., attached directly to (or by a lead to) the housing of a pacemaker, ICD or cardiac monitor, as will be described in more detail below.

The diastolic pressure (DP), which is the lowest arterial blood pressure, occurs at the end of diastole (ED in FIG. 1A), which substantially coincides with the beginning of systole. The systolic pressure (SP), which is the peak arterial blood pressure, occurs during systole, at a time between the beginning of systole and the end of systole (ES in FIG. 1A). Specific embodiments of the present invention, discussed below, determine surrogates of SP and DP based on the morphology of a PPG waveform. Based thereon, surrogates of mean arterial pressure (MAP) and/or pulse pressure (PP) can also be determined, in accordance with specific embodiments of the present invention. Surrogates of cardiac afterload (CA) can also be determined based on the morphology of a PPG waveform, in accordance with embodiments of the present invention discussed below.

Diastolic Pressure (DP)

In accordance with specific embodiments of the present invention, a surrogate of DP can be determined by determining a metric of the terminal portion of a PPG waveform. Such a metric can be referred to as a terminal metric (Tmetric). In one embodiment, a surrogate of DP is an integral from a maximum to the following minimum of the arterial PPG waveform, which is indicative of the area 212, shown in FIG. 2A. In other words, the Tmetric can be the integral from a maximum to the following minimum of the arterial PPG waveform.

Figure 2A:
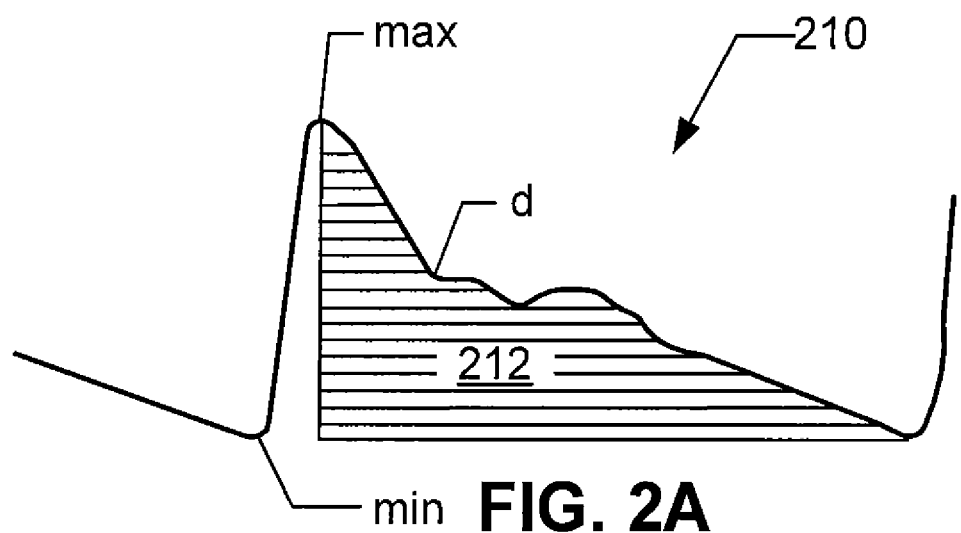
FIG. 2A illustrates a surrogate of diastolic pressure DP in the form of an integral from a maximum to the following minimum of the arterial PPG waveform.
Figure 2B:
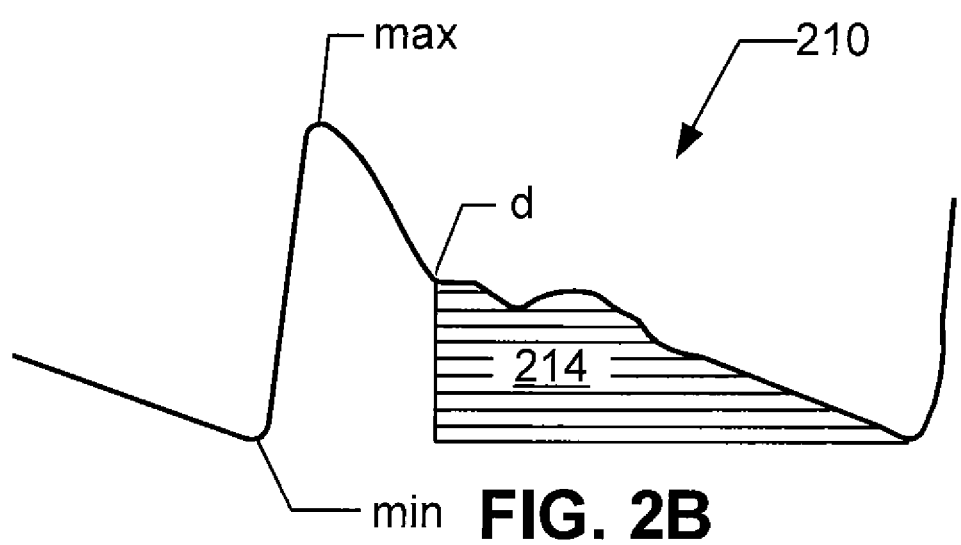
FIG. 2B illustrates a surrogate of DP in the form of an integral from a dicrotic notch to the following minimum of the arterial PPG waveform.

In another embodiment, a surrogate of DP is an integral from a dicrotic notch to the following minimum of the arterial PPG waveform, which is indicative of the area 214, shown in FIG. 2B. In other words, the Tmetric can be the integral from a dicrotic notch to the following minimum of the arterial PPG waveform.

Figure 2C:
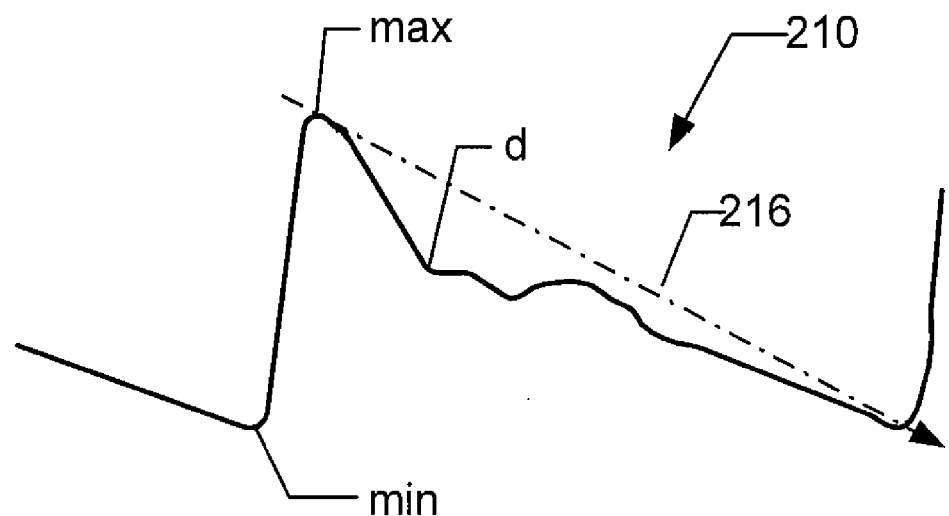
FIG. 2C illustrates a surrogate of DP in the form of the downward slope from a maximum to the following minimum of the arterial PPG waveform.

In a further embodiment, a surrogate of DP is a terminal deceleration slope (TDS) 216, which as shown in FIG. 2C, is a downward slope from a maximum to the following minimum of the arterial PPG waveform. In other words, the Tmetric can be the TDC 216.

Figure 2D:
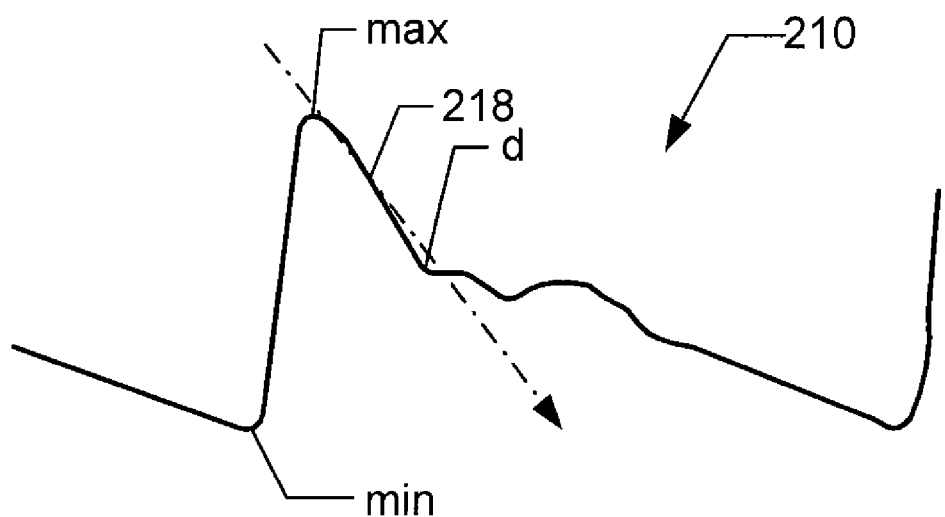
FIG. 2D illustrates a surrogate of DP in the form of the downward slope from a maximum to the following dicrotic notch of the arterial PPG waveform.

In another embodiment, a surrogate of DP is a beginning terminal deceleration slope (BTDS) 218, which as shown in FIG. 2D, is a downward slope from a maximum to the following dicrotic notch of the arterial PPG waveform. In other words, the Tmetric can be the BTDS 218.

Figure 2E:
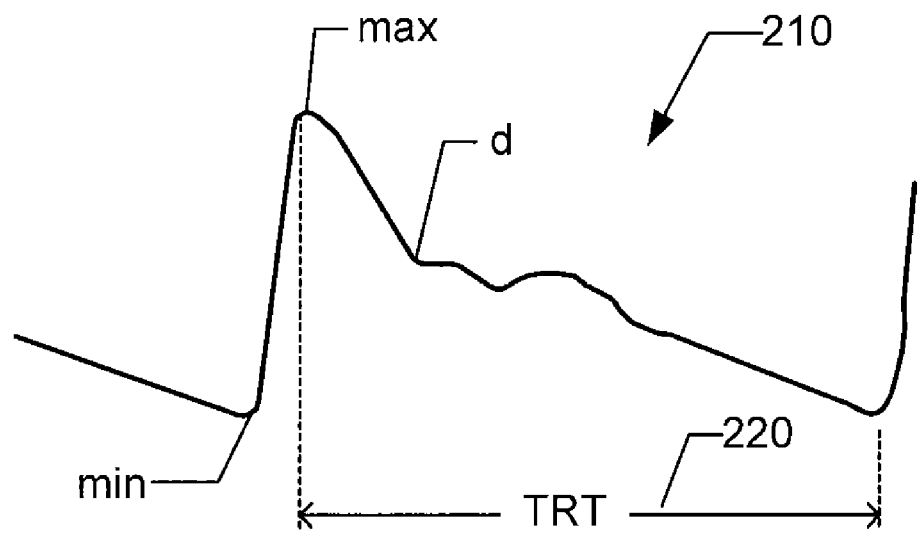
FIG. 2E illustrates a surrogate of DP in the form of the time from a maximum to the following minimum of the atrial PPG signal.

In still another embodiment, a surrogate of DP is a total relaxation time (TRT) 220, which as shown in FIG. 2E, is a time from a maximum to the following minimum of the atrial PPG signal. In other words, the Tmetric can be the TRT 220.

Figure 2F:
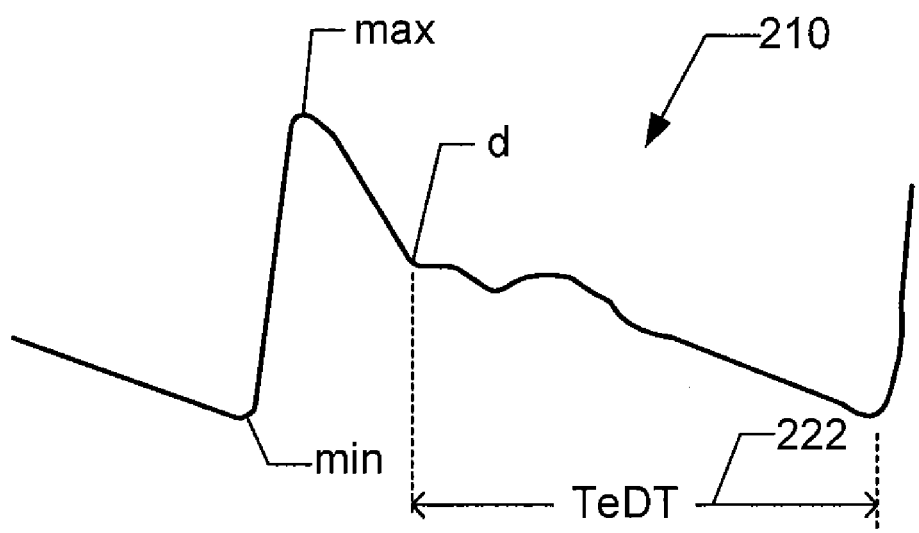
FIG. 2F illustrates a surrogate of DP in the form of the time from a dicrotic notch to the following minimum of the atrial PPG signal.

In yet another embodiment, a surrogate of DP is a terminal deceleration time (TeDT) 222, which as shown in FIG. 2F, is a time from a dicrotic notch to the following minimum of the atrial PPG signal. In other words, the Tmetric can be the TeDT 222.

Preferably, in each of the above described embodiments, the arterial PPG waveform from which the Tmetric is measured is an averaged arterial PPG waveform that is produced by averaging a plurality of cardiac cycles of a PPG signal obtained from an implanted extravascular PPG sensor. Such an averaged arterial PPG waveform should provide an improved signal to noise ratio, as compared to a non-average waveform. Additionally, depending on the time frame over which the averaged arterial PPG waveform is produced, measuring a T-metric based on an averaged arterial PPG waveform can provide a chronic measure of a surrogate of DP, as opposed to a beat-to-beat measure.

Figure 2G:
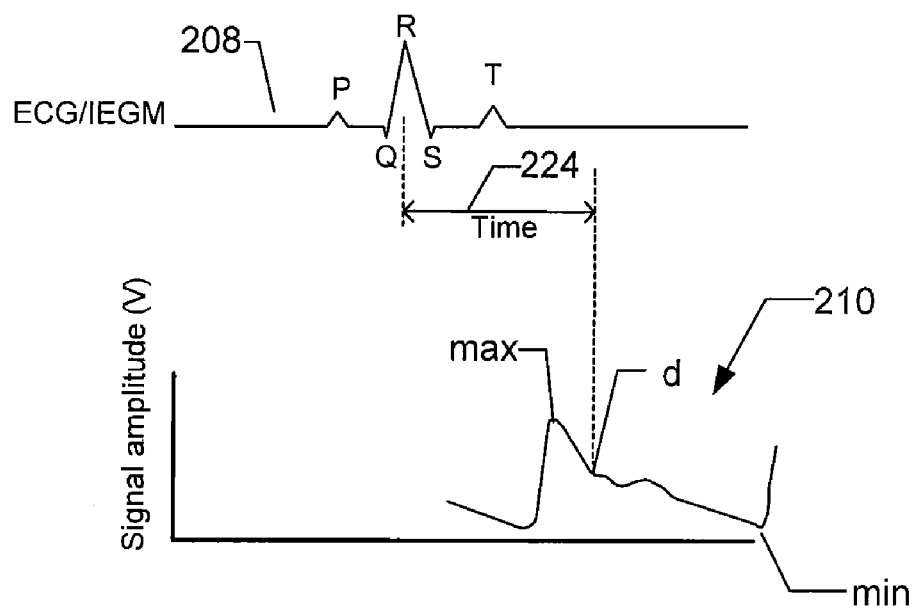
FIG. 2G illustrates a surrogate of DP in the form of the time from a ventricular depolarization (detected in a cardiac cycle of an IEGM or ECG) to a dicrotic notch (detected in a portion of an arterial PPG signal corresponding to the same cardiac cycle).

Referring to FIG. 2G, in still another embodiment, a surrogate of DP is a time 224 from a ventricular depolarization (detected in a cardiac cycle of an IEGM or ECG) to a dicrotic notch (detected in a portion of an arterial PPG signal corresponding to the same cardiac cycle).

Figure 2H:
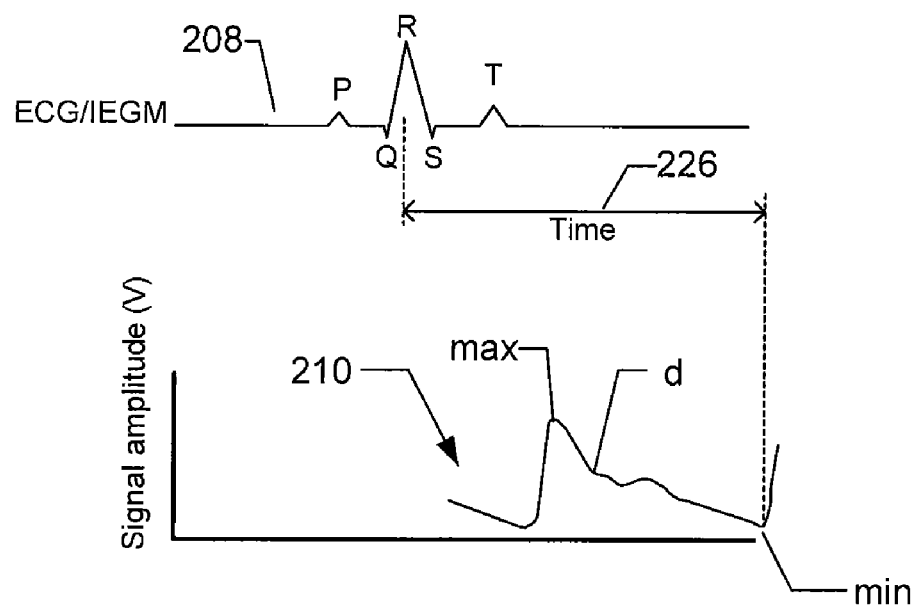
FIG. 2H illustrates a surrogate of DP in the form of the time from a ventricular depolarization (detected in a cardiac cycle of an IEGM or ECG) to a minimum (detected in a portion of an arterial PPG signal corresponding to the same cardiac cycle).

Referring to FIG. 2H, in still another embodiment, a surrogate of DP is a time 226 from a ventricular depolarization (detected in a cardiac cycle of an IEGM or ECG) to a minimum (detected in a portion of an arterial PPG signal corresponding to the same cardiac cycle).

In each of the above embodiments, the surrogates of DP do not provide actual values of DP, but rather, provide values that are believed to change as DP changes. Because of this, one or more of the above described surrogate of DP can be measured from time to time, and changes in the surrogate(s) of DP can be interpreted as changes to DP.

Figure 3A:
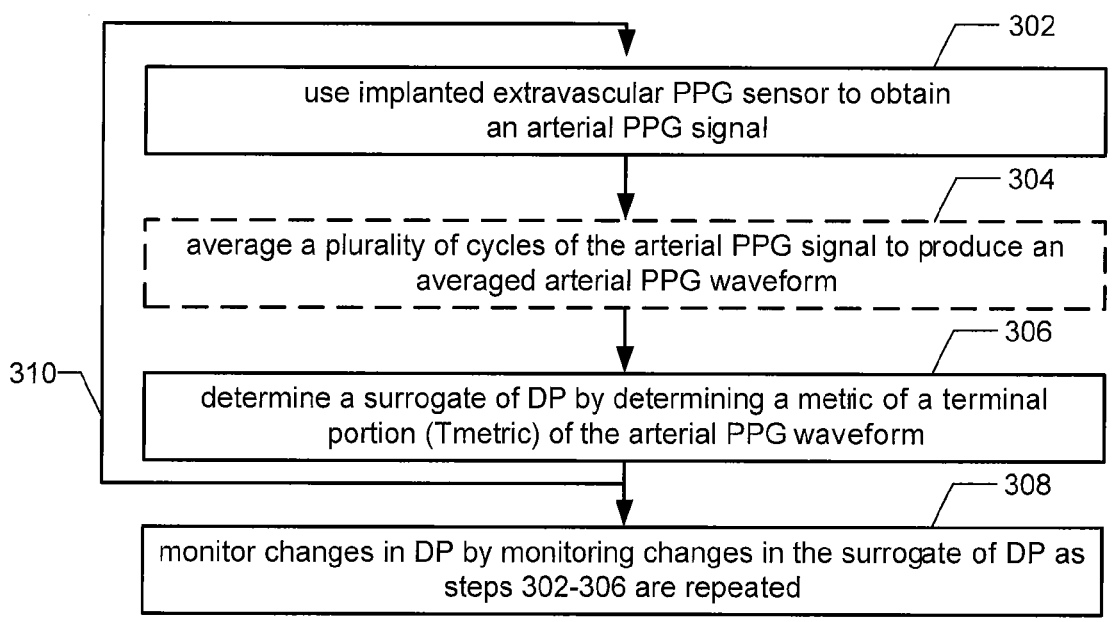
FIG. 3A is a high level flow diagram that is used to explain specific embodiments of the present invention that can be used to monitor DP.
Figure 3B:
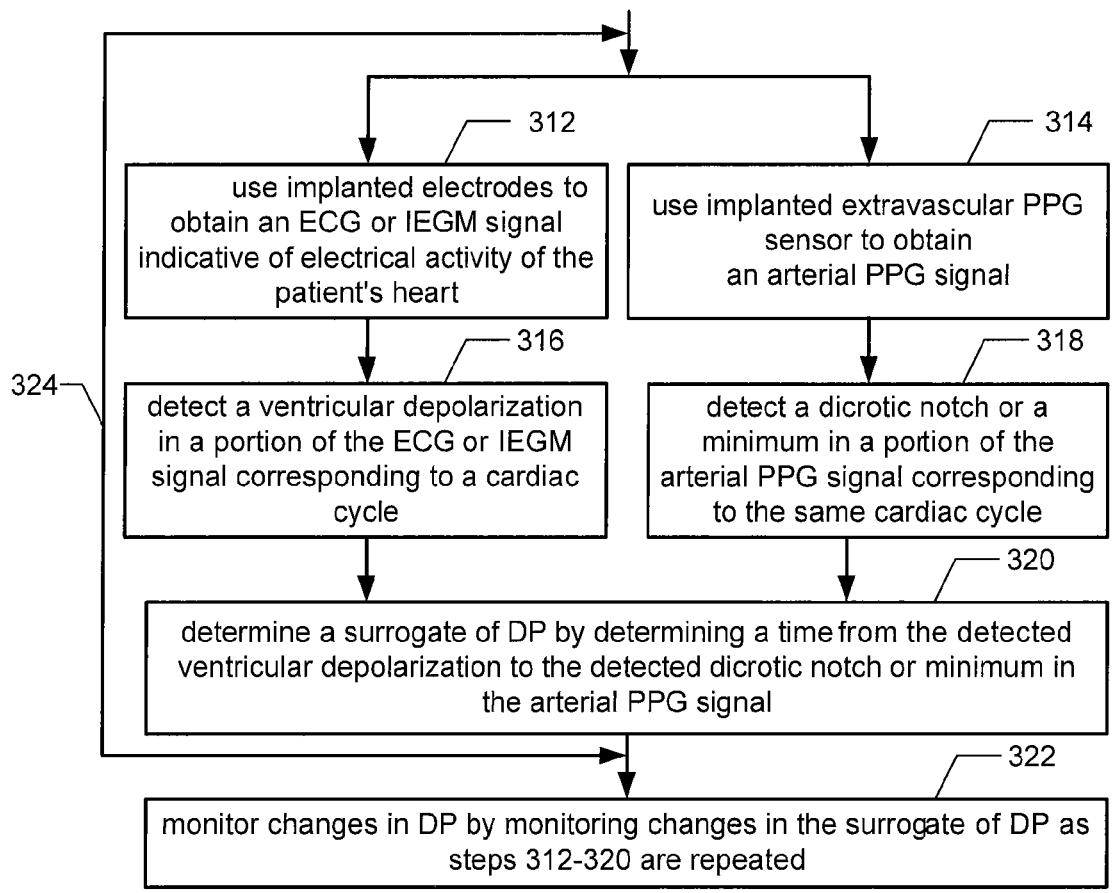
FIG. 3B is a high level flow diagram that is used to explain alternative embodiments of the present invention that can be used to monitor DP.

The above described embodiments will now be summarized with reference to the high level flow diagrams of FIG. 3A and 3B. Where embodiments of the present invention are summarized with reference to the high level flow diagrams, various algorithmic steps are summarized in individual 'blocks'. Such blocks describe specific actions or decisions that are made or carried out as the algorithm proceeds. Where a microcontroller (or equivalent) is employed, the flow diagrams presented herein provides the basis for a 'control program' that may be used by such a microcontroller (or equivalent) to effectuate the desired control of the implantable system. Those skilled in the art may readily write such a control program based on the flow diagram and other descriptions presented herein. Embodiments of the present invention are not limited to the exact order and/or boundaries of the steps shown in the flow diagrams. In fact, many of the steps can be performed in a different order than shown, and many steps can be combined, or separated into multiple steps. All such variations are encompassed by the present invention. The only time order is important is where a step acts on the results of a previous step.

Referring to FIG. 3A, at step 302, an arterial PPG signal is obtained using an implanted extravascular PPG sensor. Details of exemplary PPG sensors are provided below with reference to FIGS. 8A-8C. As mentioned above, for certain embodiments it is preferred that a plurality of cardiac cycles of the obtained PPG signal are averaged to produce a PPG waveform that is an averaged PPG waveform. This is indicated at step 304.

At step 306, a surrogate of DP is determined by determining a metric of a terminal portion (Tmetric) of the arterial PPG waveform. As explained above, Tmetrics according to embodiments of the present invention can include: an integral from a maximum to the following minimum of the arterial PPG waveform (212 in FIG. 2A); an integral from a dicrotic notch to the following minimum of the PPG waveform (214 in FIG. 2B); a terminal deceleration slope (TDS) (216 in FIG. 2C); a beginning terminal deceleration slope (BTDS) (218 in FIG. 2D); a total relaxation time (TRT) (220 in FIG. 2E); and a terminal deceleration time (TeDT) (222 in FIG. 2F).

As indicated by arrowed line 310, steps 302-306 are repeated from time to time, e.g., periodically, or in response to a triggering event. For example, steps 302-306 can be performed substantially continually, or periodically (e.g., once an hour, a day, a week, or the like). For another example, steps 302-306 can be performed aperiodically, e.g., in response to a triggering event, many examples of which are discussed below. As indicated at step 308, changes in DP are monitored based on changes in the surrogate of DP, i.e., changes in the Tmetric. In an embodiment, increases in the magnitude of the Tmetric are interpreted as increases in DP, and decreases in the magnitude of the Tmetric are interpreted as decreases in DP.

Referring now to FIG. 3B, in accordance with an embodiment of the present invention, implanted electrodes are used to obtain a signal indicative of electrical activity of the patient's heart at step 312, and an implanted extravascular PPG sensor is used to obtain an arterial photoplethysmography (PPG) signal at step 312. In accordance with specific embodiments of the present invention, an IEGM signal (e.g., similar to 108) is obtained using implanted electrodes on endocardial lead(s), which typically provide for better fidelity than an ECG signal obtained from non-implanted surface electrodes. In another embodiment, the signal obtained at step 312 is an electrocardiogram (ECG) obtained using chronically implanted extracardiac subcutaneous electrodes.

At step 316, a ventricular depolarization is detected in a portion of the ECG or IEGM signal corresponding to a cardiac cycle. A QRS complex, such as the one shown in signal 108 of FIG. 1, is indicative of ventricular depolarization. Ventricular depolarization can be detected, e.g., by detected the Q wave of the QRS complex, the R wave of the QRS complex, and/or the S wave of the QRS complex. However, since the R wave is the easiest to detect, due to its relatively large magnitude, it is practical for ventricular depolarization to be detected by detecting the R wave. Accordingly, any known or future developed technique for detecting an R wave (e.g., by peak detection or threshold crossing) can be used to detect ventricular depolarization. Exemplary techniques for detecting R waves are disclosed in U.S. Pat. No. 7,403,813, to Farazi et al., entitled "Systems and Methods for Detection of VT and VF from Remote Sensing Electrodes," which is incorporated herein by reference. Alternatively, known or future developed techniques for detecting the Q, R and/or S waves can be used to detect ventricular depolarization.

At step 318, there is a detection of a dicrotic notch or a minimum in a portion of the arterial PPG signal corresponding to the same cardiac cycle referred to in step 316. At step 320, a surrogate of DP is determined by determining a time from the detected ventricular depolarization to the detected dicrotic notch or minimum in the arterial PPG signal. A minimum peak detector circuit can be used to detect a minimum of a PPG waveform. Similarly, a local minimum peak detector circuit can be used to detect the dicrotic notch. Alternative techniques are also possible, and within the scope of the present invention.

As indicated by arrowed line 324, steps 312-320 are repeated from time to time, e.g., periodically, or in response to a triggering event. For example, steps 312-320 can be performed substantially continually, or periodically, or aperiodically, e.g., in response to a triggering event, examples of which are discussed below.

Systolic Pressure (SP)

Figure 4A:
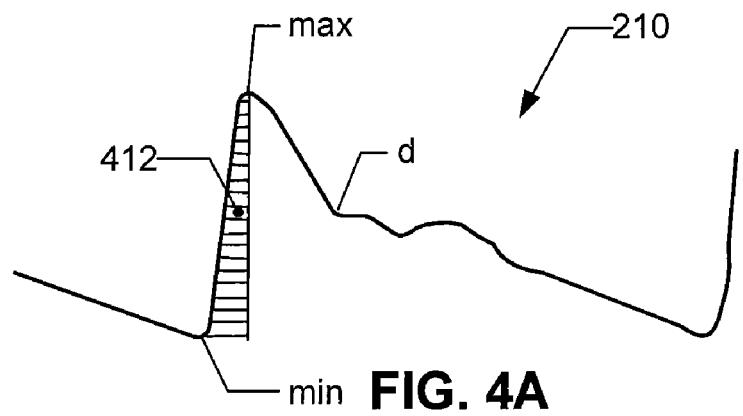
FIG. 4A illustrates a surrogate of systolic pressure (SP) in the form of an integral from a minimum to a following maximum of the arterial PPG waveform.

In accordance with specific embodiments of the present invention, a surrogate of SP can be determined by determining a metric of the initial portion of a PPG waveform. Such a metric can be referred to as an initial metric (Imetric). In one embodiment, a surrogate of SP is an integral from a minimum to a following maximum of the arterial PPG waveform, which is indicative of the area 412, shown in FIG. 4A. In other words, the Imetric can be the integral from a minimum to the following maximum of the arterial PPG waveform.

Figure 4B:
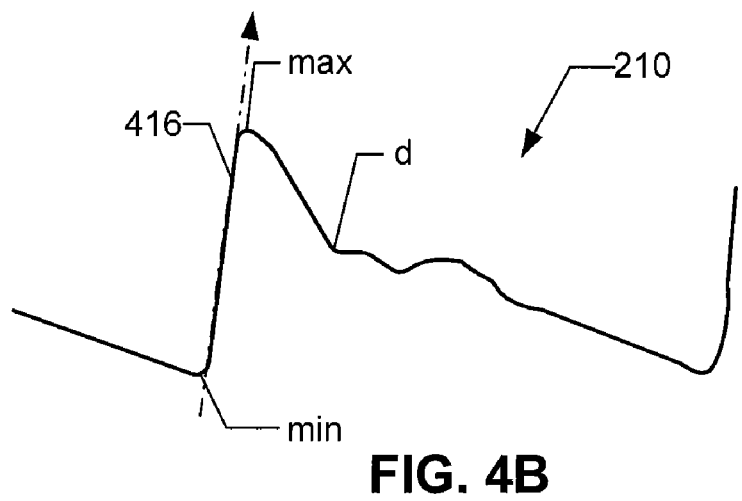
FIG. 4B illustrates a surrogate of SP in the form of an upward slope from a minimum to the following maximum of the arterial PPG waveform.

In a further embodiment, a surrogate of SP is an initial acceleration slope (IAS), which as shown in FIG. 4B, is an upward slope from a minimum to the following maximum of the arterial PPG waveform. In other words, the Imetric can be the IAS 416.

Figure 4C:
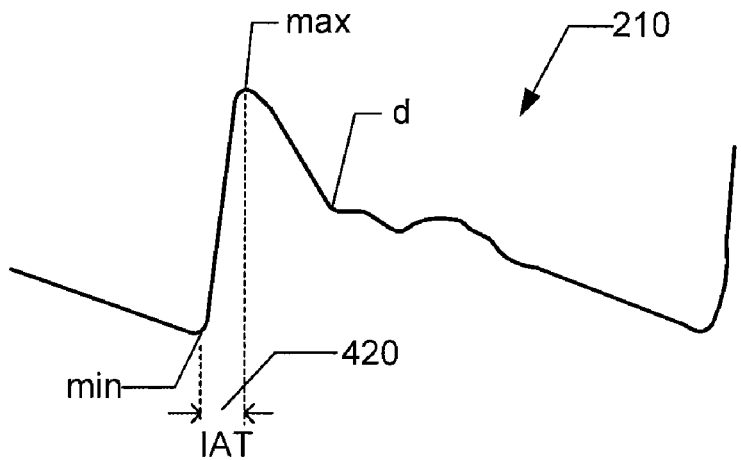
FIG. 4C illustrates a surrogate of SP in the form of the time from a minimum to the following maximum of the arterial PPG signal.

In still another embodiment, a surrogate of SP is an initial acceleration time (IAT), which as shown in FIG. 4C, is a time from a minimum to the following maximum of the arterial PPG signal. In other words, the Imetric can be the IAT 420.

In each of the above embodiments, the surrogates of SP do not provide actual values of SP, but rather, provide values that are believed to change as SP changes. It is believed that the surrogate will increase when SP increases. Because of this, one or more of the above described surrogate of SP can be measured from time to time, and changes in the surrogate(s) of SP can be interpreted as changes to SP.

Figure 5:
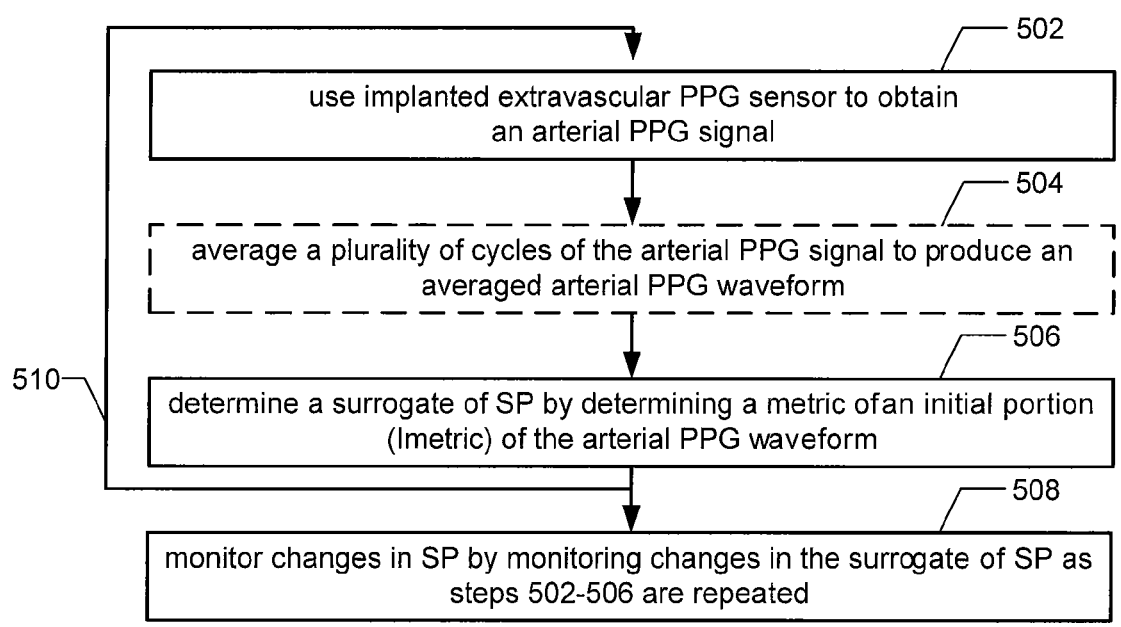
FIG. 5 is a high level flow diagram that is used to explain specific embodiments of the present invention that can be used to monitor SP.

The above described embodiments will now be summarized with reference to the high level flow diagram of FIG. 5. Referring to FIG. 5, at step 502, an arterial PPG signal is obtained using an implanted extravascular PPG sensor. As mentioned above, for certain embodiments it is preferred that a plurality of cardiac cycles of the obtained PPG signal are averaged to produce a PPG waveform that is an averaged PPG waveform. This is indicated at step 504.

At step 506, a surrogate of SP is determined by determining a metric of an initial portion (Imetric) of the arterial PPG waveform. As explained above, Imetrics according to embodiments of the present invention can include: an integral from a minimum to the following maximum of the arterial PPG waveform (412 in FIG. 4A); an initial acceleration slope (IAS) (416 in FIG. 4B); and an initial acceleration time (IAT) (420 in FIG. 4C). As indicated by arrowed line 510, steps 502-506 are repeated from time to time, e.g., periodically, or aperiodically in response to a triggering event, in similar manners as were discussed above with reference to earlier flow diagrams. As indicated at step 508, changes in SP are monitored based on changes in the surrogate of SP, i.e., changes in the Imetric. In an embodiment, increases in the magnitude of the Imetric are interpreted as increases in SP, and decreases in the Imetric are interpreted as decreases in SP.

Mean Arterial Pressure (MAP) and Pulse Pressure (PP)

As mentioned above, the systolic pressure (SP) is the peak pressure in the arteries, which occurs near the beginning of a cardiac cycle. The diastolic pressure (DP) is the lowest pressure in the arteries, which occurs at the end of the resting phase of the cardiac cycle. The pulse pressure (PP) is the difference between the systolic and diastolic pressures. The mean arterial pressure (MAP) is a weighted average of pressure throughout the cardiac cycle. In accordance with specific embodiments of the present invention, certain surrogates of DP and SP determined above, can be used together, to produce a surrogate of MAP and/or a surrogate of PP. This will be described with reference to the high level flow diagram of FIG. 6.

Figure 6:
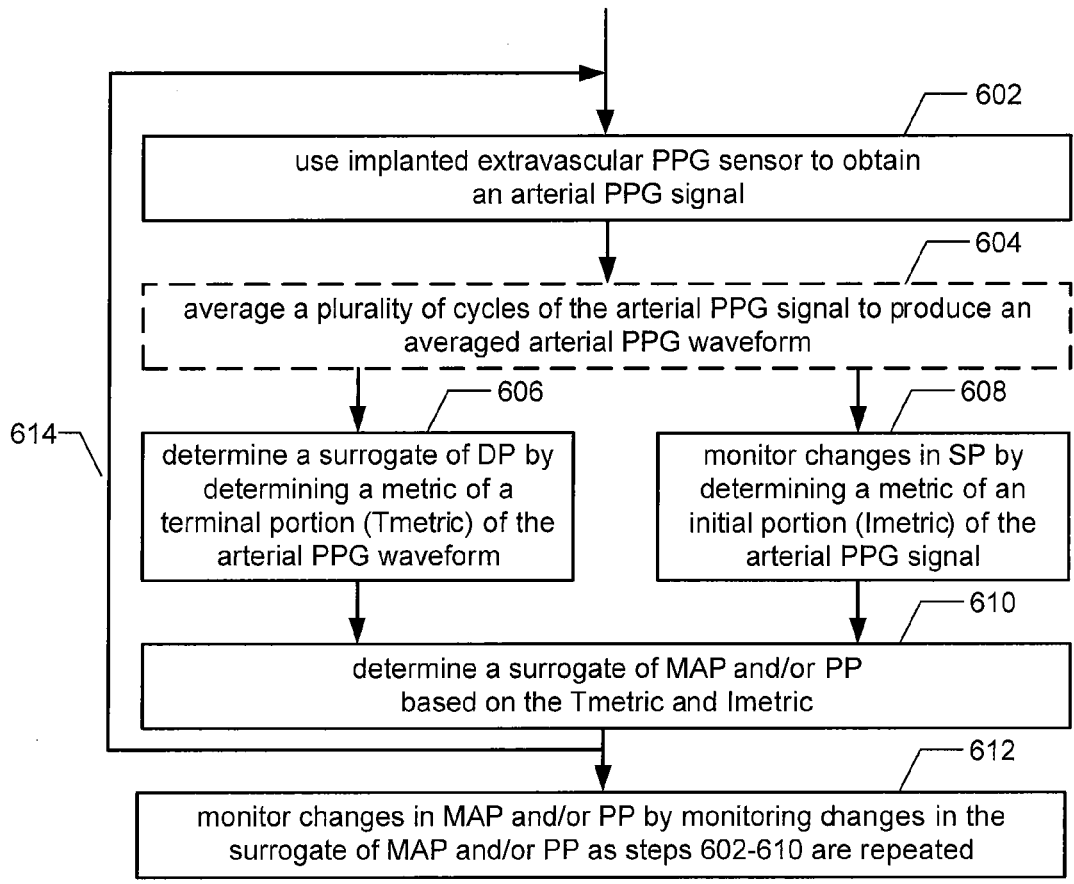
FIG. 6 is a high level flow diagram that is used to explain specific embodiments of the present invention that can be used to monitor mean arterial pressure (MAP) and/or pulse pressure (PP).

Referring to FIG. 6, steps 602 and 604 are similar to steps 302 and 304, and steps 502 and 504, and thus these steps need not be described again in detail. At step 606, a surrogate of DP is determined by determining a metric of a terminal portion (Tmetric) of an arterial PPG waveform. At step 608, a surrogate of SP is determined by determining a metric of an initial portion (Imetric) of the arterial PPG waveform. Exemplary Tmetrics and Imetrics are described in detail above.

Preferably the Tmetric and Imetric used at step 608 should correspond to one another. For example, in accordance with an embodiment, the Tmetric is an integral from a maximum to the following minimum of the arterial PPG waveform (e.g., 212 in FIG. 2A), and the Imetric is an integral from a minimum of the arterial PPG waveform to the following maximum of the PPG waveform (e.g., 412 in FIG. 4A). In another embodiment, the Tmetric is an integral from a dicrotic notch to the following minimum of the PPG waveform (e.g., 214 in FIG. 2B), and the Imetric is an integral from a minimum of the arterial PPG waveform to the following maximum of the PPG waveform (e.g., 412 in FIG. 4A). In a further embodiment, the Tmetric is a terminal deceleration slope (TDS) (e.g., 216 in FIG. 2C) or the beginning terminal deceleration slope (BTDS) (e.g., 218 in FIG. 2D), and the Imetric is an initial acceleration slope (IAS) (e.g., 416 in FIG. 4B). In still another embodiment, the Tmetric is a total relaxation time (TRT) (e.g., 220 in FIG. 2D) or the terminal deceleration time (TeDT), and the Imetric is an initial acceleration time (IAT) (e.g., 420 in FIG. 4C).

At step 610, a surrogate of MAP is determined based on the Tmetric and Imetric determined at steps 606 and 608. For example, one of the following equations can be used.

$$\text{MAP surrogate} = \tfrac{2}{3} * |\text{Tmetric}| + \tfrac{1}{3} * |\text{Imetric}|$$

or $$\text{MAP surrogate} = \tfrac{1}{2} * |\text{Tmetric}| + \tfrac{1}{2} * |\text{Imetric}|.$$

The pulse pressure (PP) reflects the difference between the maximum and minimum pressures measured (i.e., the difference between the systolic pressure and diastolic pressure). Additionally, or alternatively, at step 610, a surrogate of PP is determined based on the Tmetric and Imetric determined at steps 606 and 608. For example, the following equation can be used.

$$\text{PP surrogate} = |\text{Tmetric}| - |\text{Imetric}|.$$

As indicated by arrowed line 614, steps 602-610 are repeated from time to time, e.g., periodically, or aperiodically in response to a triggering event, in similar manners as were discussed above with reference to earlier flow diagrams. As indicated at step 612, changes in MAP and/or PP are monitored based on changes in the surrogate of MAP and/or PP. In an embodiment, increases in the magnitude of the surrogate of MAP are interpreted as increases in MAP, and decreases in the surrogate of MAP are interpreted as decreases in MAP. Similarly, increases in the magnitude of the surrogate of PP can be interpreted as increases in PP, and decreases in the surrogate of PP can be interpreted as decreases in PP.

Cardiac Afterload

Cardiac afterload (CA), also referred to as ventricular afterload as mentioned above, may be defined as the mechanical force opposing ventricular ejection. Stated another way, CA is the pressure that the chamber of the heart has to generate in order to eject blood out of the chamber. Embodiments of the present invention, which relate to implantable systems (and methods for use with implantable systems) for monitoring cardiac afterload (CA), will now be described with reference to the high level flow diagram of FIG. 7.

Figure 7:
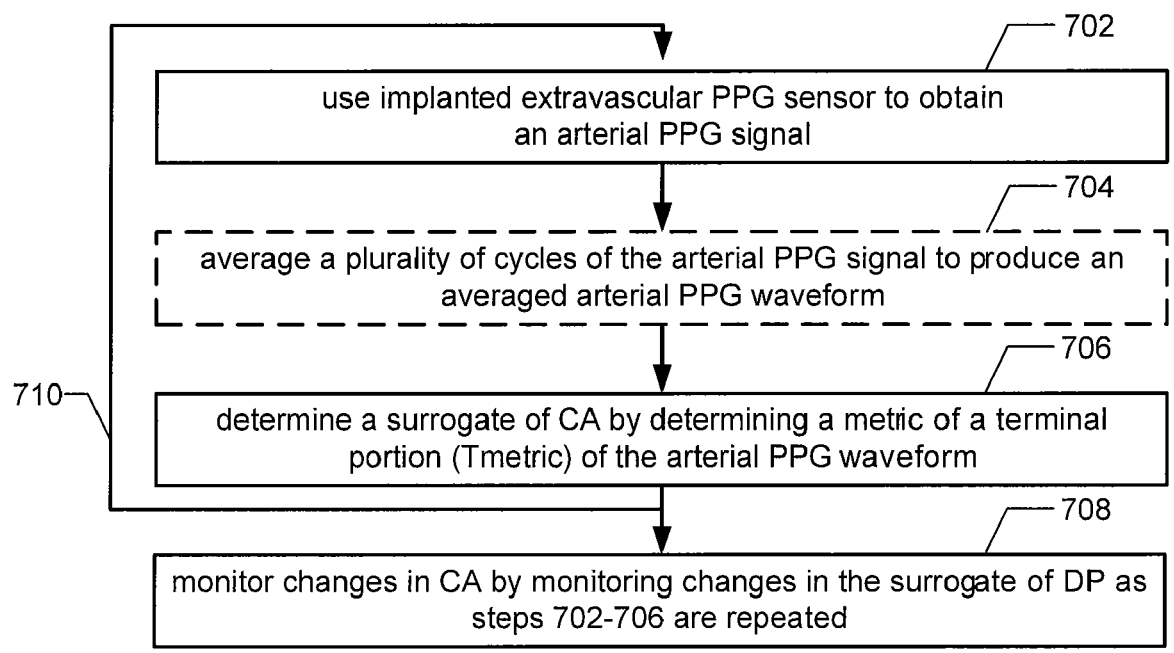
FIG. 7 is a high level flow diagram that is used to explain specific embodiments of the present invention that can be used to monitor cardiac afterload (CA).

Referring to FIG. 7, at step 702, an arterial PPG signal is obtained using an implanted extravascular PPG sensor. As mentioned above, for certain embodiments it is preferred that a plurality of cardiac cycles of the obtained PPG signal are averaged to produce a PPG waveform that is an averaged PPG waveform. This is indicated at step 704.

At step 706, a surrogate of CA is determined by determining a metric of a terminal portion (Tmetric) of the arterial PPG waveform. As explained above, Tmetrics according to embodiments of the present invention can include: an integral from a maximum to the following minimum of the arterial PPG waveform (212 in FIG. 2A); an integral from a dicrotic notch to the following minimum of the PPG waveform (214 in FIG. 2B); a terminal deceleration slope (TDS) (216 in FIG. 2C); a beginning terminal deceleration slope (BTDS) (218 in FIG. 2D); a total relaxation time (TRT) (220 in FIG. 2E); and a terminal deceleration time (TeDT) (222 in FIG. 2F). As indicated by arrowed line 710, steps 702-706 are repeated from time to time, e.g., periodically, or aperiodically in response to a triggering event, in similar manners as were discussed above with reference to earlier flow diagrams.

As indicated at step 708, changes in CA are monitored based on changes in the surrogate of CA, i.e., changes in the Tmetric. It is believed that the integral from a maximum to the following minimum of the arterial PPG waveform is directly related to CA, and thus an increase in such an integral is indicative of an increase in CA, and vise versa. It is also believed that the integral from a dicrotic notch to the following minimum of the PPG waveform is directly related to CA, and thus an increase in such an integral is indicative of an increase in CA, and vise versa. It is believed that the absolute value of the terminal deceleration slope (TDS) is inversely related to CA, and thus, a decrease in the absolute value of TDS is indicative of an increase in CA, and vise versa. It is believed that the absolute value of the beginning terminal deceleration slope (BTDS) is also inversely related to CA, and thus, a decrease in the absolute value of BTDS is indicative of an increase in CA, and vise versa. It is believed that the total relaxation time (TRT) is directly related CA, and thus, that an increase in the TRT is indicative of an increase in CA, and vise versa. It is believed that the terminal deceleration time (TeDT) is directly related CA, and thus, that an increase in the TeDT is indicative of an increase in CA, and vise versa. Details of how to determine such Tmetrics are discussed above, and thus need not be repeated again.

Exemplary Calibration Procedure

An exemplary calibration procedure (performed at implant and/or thereafter) will now be explained. During the calibration procedure, actual measures of arterial blood pressure, including SP and DP, are measured along with surrogates of the same (e.g., Imetrics and Tmetrics). The actual measure of the patient's SP and DP can be obtained, e.g., using a non-invasive auscultatory or oscillometric techniques, or an invasive intravascular cannula method, or any other acute technique. For a more specific example, actual arterial pressure measurements (SP and DP) can be measured using a high fidelity micrometer-tipped pressure catheter (e.g., model 4F, SPC-340, available from Millar Instruments, Texas), which is placed in the ascending aorta via a carotid arteriotomy. Other techniques are also possible, and within the scope of the present invention.

During calibration, while actual values of SP are being determined for various Imetric values, actual values of DP can also be determined for various Tmetric values. This will enable a patient specific correlation factor M (and possibly also a) to be determined during the calibration procedure. For example, estimates of actual values of DP and SP can be determined by using such correlation factors, e.g., $DP = M_1 * \text{Tmetric}_1$ (or $DP = M_1 * \text{Tmetric}_1 + \sigma_1$) and/or $SP = M_2 * \text{Imetric}_2$ (or $SP = M_2 * \text{Tmetric}_2 + \sigma_2$). Since actual values of DP and SP can be obtained during calibration (at implant and/or thereafter), and values of Tmetrics and Imetrics can be measured during calibration, the patient specific correlation factor M (and possibly also σ) can be easily determined. Other formulas are also possible, and could be derived by determining actual values of DP and/or SP for various different values and types of Tmetrics and/or Imetrics. After implant, an algorithm or look-up table can be used to calculate DP, SP, MAP and/or PP based on Tmetrics and/or Imetrics. Once SP and DP are determined, mean arterial pressure (MAP) can also be determined. For example, the equation MAP=⅓ SP+⅔ DP can be used. Alternatively, the equation MAP=(SP+DP)/2 can be used. Use of other equations is also within the scope of the present invention.

In another calibration procedure, actual values of CA can be determined for various Tmetric values. This will enable a patient specific correlation factor M (and possibly also a) to be determined during the calibration procedure. For example, estimates of actual values of CA can be determined by using such correlation factors, e.g., $CA=M_3*Tmetric_3$ (or $CA=M_3*Tmetric_3+\sigma_3$). Since actual values of CA can be obtained during calibration (at implant and/or thereafter), and values of Tmetrics can be measured during calibration, the patient specific correlation factor M (and possibly also a) can be easily determined. Other formulas are also possible, and could be derived by determining actual values of CA for various different values and types of Tmetrics. After implant, an algorithm or look-up table can be used to calculate CA based on Tmetrics.

Uses of Embodiments of the Present Invention

Because an implanted sensor and in some embodiments implanted electrodes are used to obtain the various arterial pressure measurements and/or CA measurements, a patient's arterial blood pressure and/or CA can be monitored on a chronic basis. Thus, arterial blood pressure and/or CA can be tracked to monitor a patient's worsening (or improving) cardiac disease state, and to trigger alerts and/or titration of blood pressure medications. Additionally, arterial blood pressure and/or CA measurements can be used as a measure of hemodynamic function, and thus used in a closed loop for hemodynamic optimization (e.g., A-V delay, VV delay, and/or pacing rate optimization).

Embodiments of the present invention can be implemented within a pacemaker or ICD system, or as part of an implantable monitor that does not pace and/or shock a patient's heart. Additional details of such embodiments are provided below.

In accordance with specific embodiments of the present invention, arterial blood pressure information such as the surrogates of DP, SP, MAP and/or PP, and/or surrogates of CA, and potentially other information is stored within memory of the implantable system for later analysis within the device and/or for later transmission to an external device. Such an external device (e.g., an external programmer or external monitor) can then be used to analyze such data.

In accordance with specific embodiments of the present invention, an alarm can be triggered based on comparisons of the surrogates of SP, the surrogates of DP, the changes in SP and/or the changes in DP to corresponding thresholds. Such an alarm can be part of an implanted system. Alternatively, an implanted system can trigger a non-implanted alarm of a non-implanted system. In still other embodiments, where arterial pulse pressure information is transmitted (e.g., via telemetry) to an external device, a non-implanted alarm can be triggered based on comparisons of the surrogates of SP, the surrogates of DP, the changes in SP and/or the changes in DP, received by the non-implanted device, to corresponding thresholds. Surrogates of SP and DP can be used to determine values of indicative of MAP, and corresponding MAP thresholds can be used to trigger alarms or the like.

In accordance with specific embodiments of the present invention, an alarm can be triggered based on comparisons of the surrogates of CA, and/or the changes in the surrogates of CA to corresponding thresholds. Such an alarm can be part of an implanted system. Alternatively, an implanted system can trigger a non-implanted alarm of a non-implanted system. In still other embodiments, where CA information is transmitted (e.g., via telemetry) to an external device, a non-implanted alarm can be triggered based on comparisons of the surrogates of CA, received by the non-implanted device, to corresponding thresholds.

In accordance with specific embodiments of the present invention, the methods described with reference to the flow diagram can be repeated from time-to-time, to thereby track changes in SP, DP, MAP, PP and/or CA. For example, steps of a flow diagram can be performed periodically (e.g., once a minute, hour, day, week, or the like). The surrogates of SP, DP, MAP, PP and/or CA can be compared in real time to corresponding thresholds. Alternatively, or additionally, surrogates of SP, DP, MAP, PP and/or CA can be stored in memory of the implanted system. Such stored values can be analyzed by the implanted system and/or transmitted (e.g., via telemetry) to an external system (e.g., external programmer and external monitor) and analyzed by the external system. Use of various thresholds can be used to trigger alarms and/or therapy, as will be described below.

Depending on the frequency, periodic monitoring of arterial blood pressure and/or CA may be costly in terms of energy, memory and/or processing resources. Accordingly, it may be more efficient to trigger the performance of certain steps upon detection of an event, such as a specific activity, or lack thereof, and/or a specific posture of the patient. For example, an activity sensor and/or posture sensor can be used to trigger the performance of steps of a flow diagram. For example, steps can be triggered when it is detected that a patient is inactive and lying down. Additionally, or alternatively, steps can be triggered when a patient is upright and walking. In still other embodiments, steps can be triggered to occur, at specific intervals following a patient changing their posture (e.g., assuming an upright posture) and/or activity level. For example, following a triggering event, surrogates of arterial blood pressure and/or CA can be determined once a minute for 10 minutes, or at 1 minute, 2 minutes, 5 minutes and 10 minutes after the triggering event. Of course, other variations are also possible, and within the scope of the present invention. It may also be that one or more specific step, such as step 312, is performed substantially continually (e.g., because the signals obtained at step 312 are also used for pacing, arrhythmia detection, and the like), but other steps are only performed in response to a triggering event, such as those discussed above.

To detect posture and/or activity, an implantable system can include a sensor, which can detect a patient's posture and/or level of activity. The sensor can be, e.g., a DC-coupled 3-dimensional accelerometer as described in U.S. Pat. No. 6,658,292 (Kroll et al), a multi-axis DC accelerometer as described in U.S. Pat. No. 6,466,821 (Pianca et al), or an external field sensor as described in U.S. Pat. No. 6,625,493 (Kroll et al), each of which are incorporated herein by reference. Such sensors are able to distinguish among different static positions. In addition, since the sensors can detect motion, they can be used to distinguish between a static vertical position, such as sitting, and a standing position, which due to the dynamics of balance is associated with subtle motion that is not present while sitting. In this way an implantable system, using one of the above mentioned sensors or other sensing modality, can detect a change in body position (i.e., posture), which can be used as a trigger to perform specific methods of the present invention described below.

It is normal for there to be a normal circadian variation in arterial blood pressure values and cardiac afterload, and thus also in surrogates of SP, DP, MAP, PP and CA. For example, a drop in such values when a patient is sleeping, at rest and/or supine is normal. However, a drop in such values when a patient is active, or upright, or within a short period of a patient assuming an upright posture, is abnormal. Implanted activity and/or posture sensors can thus be used to assist in defining when an alarm or the like should be triggered. For example, a posture sensor can be used to trigger the monitoring of arterial blood pressure values when a patient assumes an upright posture. In this manner, such monitoring can be used to determine whether a drop in blood pressure within a specific amount of time (e.g., 10 minutes), following the patient assuming of an upright position, exceeds a specified threshold. Such a threshold can be, e.g., an absolute value or a percentage. In specific embodiments, the SP, DP, MAP, PP and/or CA thresholds to which determined surrogates of SP, DP, MAP, PP and/or CA are compared can be based on the activity and/or posture of the patient.

Where at least some of steps are triggered in response to detection of various different activity and/or posture states, information about the patient's activity and/or posture can also be stored along with the arterial blood pressure and/or CA information, so that such information can be correlated. In other words, there could be a cross-correlation of arterial blood pressure values and/or CA with levels of activity and/or posture.

Additionally, or alternatively, the implantable system can also monitor for episodes and degrees of myocardial ischemia, and there could be a cross-correlation of arterial blood pressure values and/or CA with degrees of ischemia (as well as with levels of activity and/or posture). This can be useful, e.g., for determining the seriousness associated with ischemic episodes. For example, severe ischemia associated with a drop in arterial blood pressure at low levels of activity is more serious than a mild degree of ischemia with no drop in blood pressure at high levels of activity.

In specific embodiments, the implanted system can detect myocardial ischemic events based on the ECG/IEGM signals, e.g., obtained at step 312. For example, known techniques can be used that perform ST-segment shift analysis to determine if there is a deviation of the ST-segment from a baseline (e.g., a PQ segment baseline), and detect myocardial ischemic events when the deviation is beyond a threshold. Other techniques are also possible. The precise technique used to detect episodes of myocardial ischemia are not important to the present invention. Rather, what is important is that episodes of myocardial ischemia can be detected, so that such information can be correlated with arterial blood pressure information, and preferably information showing such correlations can be stored. For example, the implantable system can store, in memory, arterial blood pressure data (obtained using embodiments of the present invention) corresponding to the period immediately prior to, during and subsequent to a detected myocardial ischemic episode. The implantable device can also store data that identifies the ST-segment level during various portions of an episode (e.g., at onset of the ischemia, the peak of the ischemia and the termination of the ischemia), the time of the ischemic episodes (at onset, at peak and/or at termination), the duration of the episode, as well as any other type of information that a physician may deem useful. U.S. Pat. Nos. 6,112,116; 6,272,379; and 6,609,023 (all to Fischell et al.), which are incorporated herein by reference, provide exemplary additional details of the types of data that can be stored in response to the detection of a myocardial ischemic episode, and how such data can be efficiently and effectively stored. Additionally, corresponding arterial blood pressure and/or CA information, such as surrogates of SP, DP, MAP, PP and/or CA can also be stored. This would enable the implantable system, or an external system and/or physician (which receives the information from the implantable system) to analyze how such conditions are inter-related.

Accordingly, embodiments of the present invention can be used to determine, or assist with the determination of, whether there is a correlation between levels of arterial blood pressure, levels of CA, levels of activity and/or posture, and myocardial ischemic episodes experienced by a patient. Such information will enable a medical practitioner to analyze whether ischemic episodes that the patient experienced may have precipitated changes in arterial blood pressure, CA, posture and/or activity.

In accordance with specific embodiments of the present invention, measures of arterial blood pressure, including surrogates of SP, DP, MAP, PP and/or CA, can be used for pacing interval optimization, as well as pacing rate optimization. Exemplary pacing intervals include, but are not limited to, atrio-ventricular (RA-RV) delay, interventricular (RV-LV) delay, interatrial (RA-LA) delay and intraventricular (RV1-RV2 or LV1-LV2) delay. This can include adjusting the pacing interval(s) to attempt to maintain the patient's arterial blood pressure at a specified level(s). The specified level(s) can be an optimal level(s), e.g., as specified by a physician. In specific embodiments, this can include increasing or decreasing specific pacing intervals, or combinations thereof, to attempt to increase or decrease surrogates of arterial blood pressure and/or CA. In other words, measures of arterial blood pressure, determined in accordance with embodiments of the present invention, can be used for closed loop adjustments of pacing parameters.

More generally, measures of arterial blood pressure and/or CA, obtained in accordance with embodiments of the present invention can be used to assess the hemodynamic status of a patient. This can include tracking a patient's cardiac disease state, including but not limited to, heart failure. For example, increases in measures of arterial blood pressure and/or CA over time can be interpreted as a worsening of a heart failure condition Measures of arterial blood pressure, obtained using embodiments of the present invention, can be used for arrhythmia discrimination, including tachyarrhythmia classification. For example, it is believed that before the onset of a tachyarrhythmia, there will be a detectable drop in arterial blood pressure (e.g., DP, SP and/or MAP). If the patient is experiencing an atrial tachyarrhythmia, it is believed that the arterial blood pressure will return to normal levels as the tachyarrhythmia progresses. In contrast, if the patient is experiencing a ventricular tachyarrhythmia, it is believed that the arterial blood pressure will remain low during the ventricular tachyarrhythmia. Accordingly, surrogates of arterial blood pressure can be used to distinguish atrial tachyarrhythmias from ventricular tachyarrhythmias.

Surrogates of arterial blood pressure can also be used to classify a tachyarrhythmia as either hemodynamically stable or unstable. For example, where arterial blood pressure generally stays within an acceptable range during a tachyarrhythmia, the tachyarrhythmia can be considered hemodynamically stable. In contrast, where arterial blood pressure significantly drops (or increases) due to the tachyarrhythmia, the tachyarrhythmia can be considered hemodynamically unstable. Such determinations of hemodynamic stability can be used to enable, adjust and/or abort certain stimulation therapies, including anti-tachycardia pacing (ATP) and/or shock therapy.

In the past, measures of arterial blood pressure have not generally been available before, at the onset, and during the progression of spontaneous tachyarrhythmias. By monitoring surrogates of arterial blood pressure, using embodiments of the present invention, additional information about the relationships between arterial blood pressure and tachyarrhythmias can be obtained. Such information can be very useful for detecting the onset of tachyarrhythmias, for possibly determining the cause of specific tachyarrhythmias, and for selecting, adjusting and/or aborting specific types of therapy.

Exemplary Implantable System

Figure 8A:
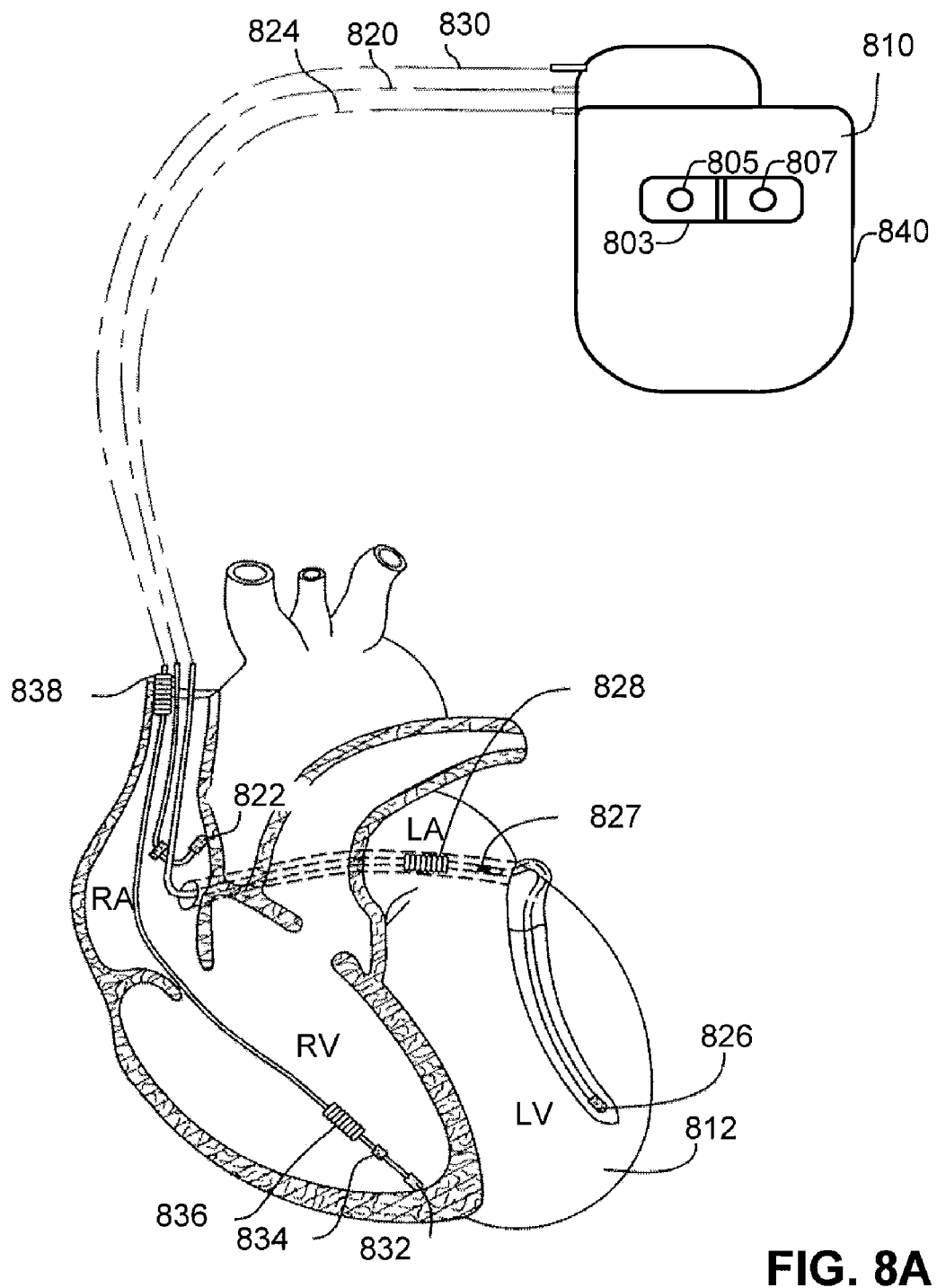
FIG. 8A illustrates an exemplary implantable stimulation device that includes a PPG sensor, and which can be used to perform embodiments of the present invention.
Figure 8B:
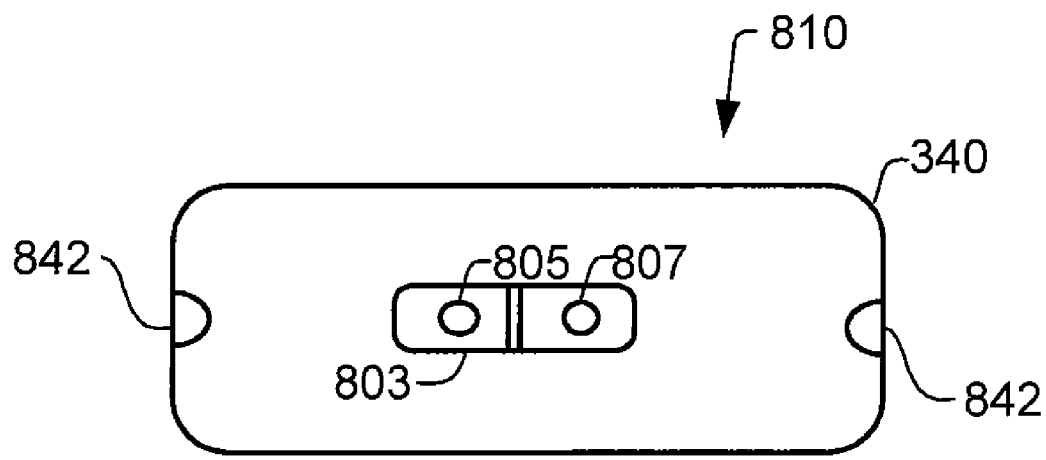
FIGS. 8B and 8C illustrates exemplary implantable monitoring devices that include a PPG sensor, and which can be used to perform embodiments of the present invention.

FIGS. 8A and 8B will now be used to describe an exemplary implantable system that can be used to determine surrogates of arterial blood pressure, in accordance with embodiments of the present invention. Referring to FIG. 8A, the implantable system is shown as including an implantable stimulation device 810, which can be a pacing device and/or an implantable cardioverter defibrillator. The device 810 is shown as being in electrical communication with a patient's heart 812 by way of three leads, 820, 824 and 830, which can be suitable for delivering multi-chamber stimulation and shock therapy. The leads can also be used to obtain IEGM signals, for use in embodiments of the present invention. Instead of having leads with electrodes attached to the heart, it is also possible that subcutaneous electrodes can be used to obtain ECG signals. In still other embodiments, it's possible that the electrodes are located on the housing of the implantable device 810, and that such electrodes are used to obtain subcutaneous ECG signals. In this latter embodiment, the device 810 may not be capable of pacing and/or defibrillation, but rather, the implantable device 810 can be primarily for monitoring purposes.

The implantable system is also shown as including an implantable photoplethysmography (PPG) sensor 803 that can be used to produce a PPG signal, similar to signal 110 shown in FIGS. 1A and 1B. Referring to FIG. 8A, the PPG 803 sensor includes a light source 805 and a light detector 807. The light source 805 can include, e.g., at least one light-emitting diode (LED), incandescent lamp or laser diode. The light detector 807 can include, e.g., at least one photoresistor, photodiode, phototransistor, photodarlington or avalanche photodiode. Light detectors are often also referred to as photodetectors or photocells.

The light source 805 outputs light that is reflected or backscattered by surrounding patient tissue, and reflected/backscattered light is received by the light detector 807. In this manner, changes in reflected light intensity are detected by the light detector, which outputs a signal indicative of the changes in detected light. The output of the light detector can be filtered and amplified. The signal can also be converted to a digital signal using an analog to digital converter, if the PPG signal is to be analyzed in the digital domain. Additional details of exemplary implantable PPG sensors are disclosed in U.S. Pat. Nos. 6,409,675 and 6,491,639, both entitled "Extravascular Hemodynamic Sensor" (both Turcott), which are incorporated herein by reference.

A PPG sensor can use a single wavelength of light, or a broad spectrum of many wavelengths. In the alternate embodiments, the light source can be any source of radiant energy, including laserdiode, heated filament, and ultrasound transducer. The detector can be any detector of radiant energy, including phototransistor, photodetector, ultrasound transducer, piezoelectric material, and thermoelectric material.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled-"Methods and Devices for Vascular Plethysmography via Modulation of Source Intensity," (Turcott), which is incorporated herein by reference.

The PPG sensor 803 can be attached to a housing 840 of an implantable device, which as mentioned above can be, e.g., a pacemaker and/or an implantable cardioverter-defibrillator (ICD), or a simple monitoring device. Exemplary details of how to attach a sensor module to an implantable cardiac stimulation device are described in U.S. patent application Ser. No. 10/913,942, entitled "Autonomous Sensor Modules for Patient Monitoring" (Turcott et al.), filed Aug. 4, 2004, which is incorporated herein by reference. It is also possible that the PPG sensor 803 be integrally part of the implantable cardiac stimulation device 810. For example, the PPG sensor 803 can be located within the housing 840 of an ICD (or pacemaker) that has a window through which light can be transmitted and detected. In a specific embodiment, the PPG sensor 803 has a titanium frame with a light transparent quartz window that can be welded into a corresponding slot cut in the housing of the ICD. This will insure that the ICD enclosure with the welded PPG sensor will maintain a hermetic condition.

Where the PPG sensor 803 is incorporated into or attached to a chronically implantable device 810, the light source 805 and the light detector 807 can be mounted adjacent to one another on the housing or header of the implantable device. The light source 805 and the light detector 807 are preferably placed on the side of the implantable device 810 that, following implantation, faces the chest wall, and are configured such that light cannot pass directly from the source to the detector. The placement on the side of the device 810 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 805 and the light detector 807 can be placed on the face of the device 810 that faces the skin of the patient.

The implantable PPG sensor 803 outputs a PPG signal similar to signal 110 shown in FIGS. 1A and 1B. More specifically, the output of the light detector 805 can be an analog signal that resembles signal 110. Such a signal can be filtered and/or amplified as appropriate, e.g., to remove respiratory affects on the signal, and the like. Additionally, the signal can be digitized using an analog to digital converter. Based on the PPG signal (and in some embodiments an ECG or IEGM obtained using implanted electrodes) surrogates of DP, SP, MAP, PP and/or CA can be determined, in accordance with embodiments of the present invention, as explained above.

Still referring to FIG. 8A, to sense atrial cardiac signals and to provide right atrial chamber stimulation therapy, the device 810 is coupled to an implantable right atrial lead 820 having at least an atrial tip electrode 822, which typically is implanted in the patient's right atrial appendage. To sense left atrial and ventricular cardiac signals and to provide left-chamber pacing therapy, the device 810 is coupled to a "coronary sinus" lead 824 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 824 is designed to receive atrial and ventricular cardiac signals and to deliver left ventricular pacing therapy using at least a left ventricular tip electrode 826, left atrial pacing therapy using at least a left atrial ring electrode 827, and shocking therapy using at least a left atrial coil electrode 828.

The device 810 is also shown in electrical communication with the patient's heart 812 by way of an implantable right ventricular lead 830 having, in this embodiment, a right ventricular tip electrode 832, a right ventricular ring electrode 834, a right ventricular (RV) coil electrode 836, and an SVC coil electrode 838. Typically, the right ventricular lead 830 is transvenously inserted into the heart 812 so as to place the right ventricular tip electrode 832 in the right ventricular apex so that the RV coil electrode 836 will be positioned in the right ventricle and the SVC coil electrode 838 will be positioned in the superior vena cava. Accordingly, the right ventricular lead 830 is capable of receiving cardiac signals and delivering stimulation in the form of pacing and shock therapy to the right ventricle.

Figure 8C:
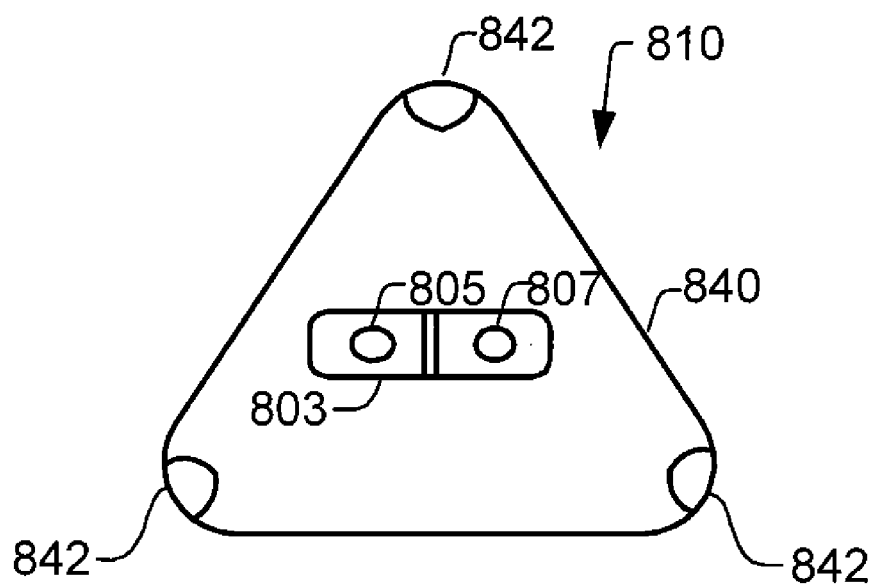

FIG. 8B illustrates an alternative embodiment of the implantable device 810. Here a housing 840 of the device is shown as small, thin, and oblong, with smooth surfaces and a physiologic contour which minimizes tissue trauma and inflammation. The oblong geometry of the housing 840 is desirable because it maximizes separation of electrodes 842 and prevents rotation of the monitor within the tissue pocket, thereby allowing interpretation of morphology features in an ECG sensed using electrodes 842. Two ECG electrodes 432 are shown, however more can be present. In the alternate embodiment illustrated in FIG. 8C, three ECG electrodes 842 are present, one at each apex of the triangle formed by the device housing 840. These three electrodes allow the three standard surface ECG leads I-III to be approximated. In another embodiment, four or more ECG electrodes might be used, with each orthogonal electrode pair providing orthogonal ECG signals. Alternatively, an embodiment lacking ECG electrodes is possible. A further alternative has a single ECG electrode with the monitor housing acting as the other electrode in the pair. U.S. Pat. No. 6,409,675, which was incorporated above by reference, provides some additional details of an implantable monitor that includes ECG electrodes on its housing and a PPG sensor. FIGS. 8B and 8C show that the implantable device 810 also include a PPG sensor 803.

Figure 9:
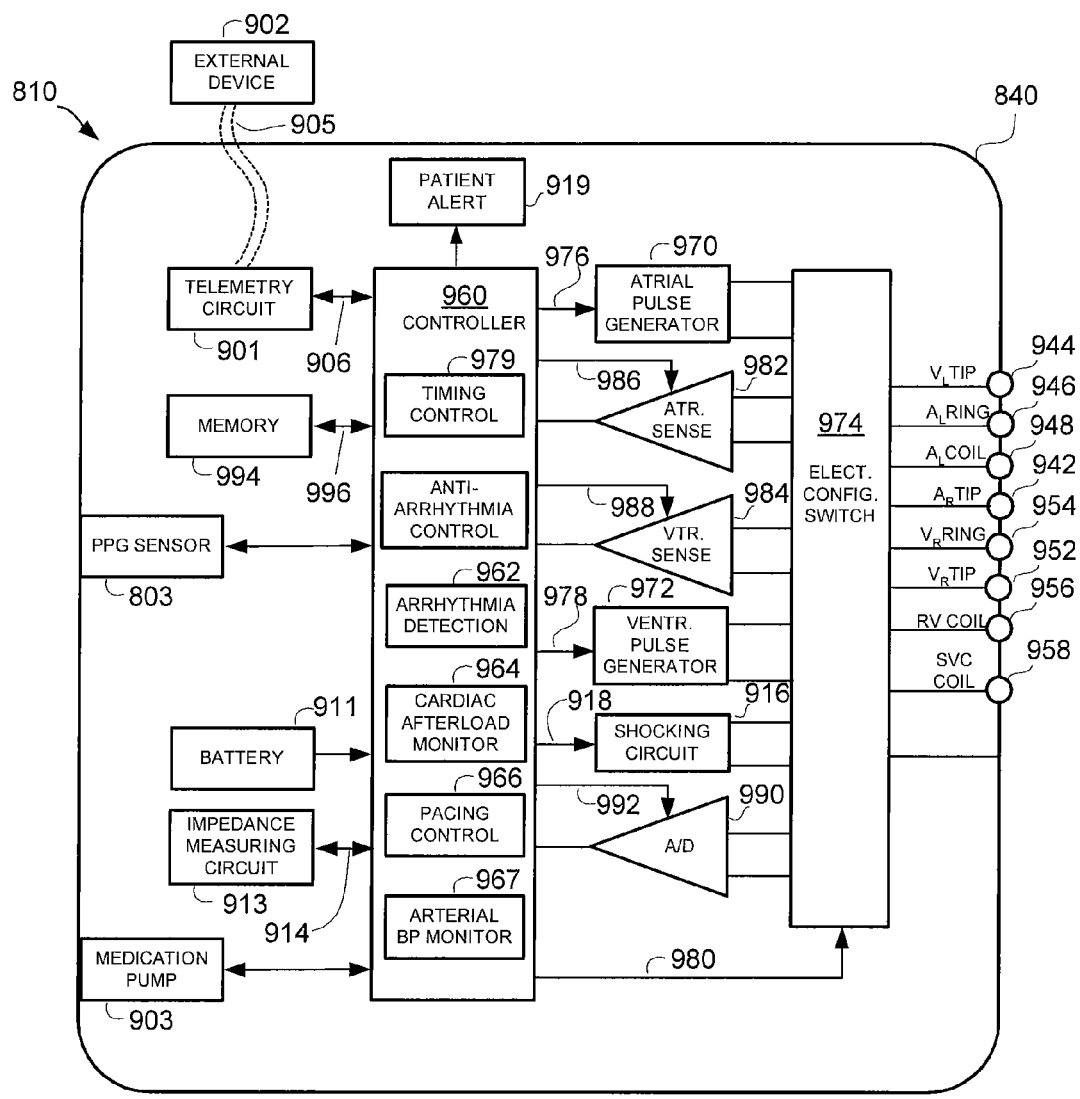
FIG. 9 is a simplified block diagram that illustrates possible components of the implantable devices shown in FIGS. 8A-8C.

FIG. 9 will now be used to provide some exemplary details of the components of the implantable devices 810. Referring now to FIG. 9, each of the above implantable devices 810, and alternative versions thereof, can include a microcontroller 960. As is well known in the art, the microcontroller 960 typically includes a microprocessor, or equivalent control circuitry, and can further include RAM or ROM memory, logic and timing circuitry, state machine circuitry, and I/O circuitry. Typically, the microcontroller 960 includes the ability to process or monitor input signals (data) as controlled by a program code stored in a designated block of memory. The details of the design of the microcontroller 960 are not critical to the present invention. Rather, any suitable microcontroller 960 can be used to carry out the functions described herein. The use of microprocessor-based control circuits for performing timing and data analysis functions are well known in the art. In specific embodiments of the present invention, the microcontroller 960 performs some or all of the steps associated with determining surrogates of arterial blood pressure, determining surrogates of CA, detecting episodes of myocardial ischemia, performing pacing interval optimization, etc. Additionally, the microcontroller 960 may detect arrhythmias, and select and control delivery of anti-arrhythmia therapy.

Representative types of control circuitry that may be used with the invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within the pacing device and their inter-relationship, see U.S. Pat. No. 4,788,980 (Mann et al.). The '052, '555, '298 and '980 patents are incorporated herein by reference.

Depending on implementation, the device 810 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, where the implantable device is a monitor that does not provide any therapy, it is clear that many of the blocks shown may be eliminated.

The housing 840, shown schematically in FIG. 9, is often referred to as the "can", "case" or "case electrode" and may be programmably selected to act as the return electrode for all "unipolar" modes. The housing 840 may further be used as a return electrode alone or in combination with one or more of the coil electrodes, 828, 836 and 838, for shocking purposes. The housing 840 can further include a connector (not shown) having a plurality of terminals, 942, 944, 946, 948, 952, 954, 956, and 958 (shown schematically and, for convenience, the names of the electrodes to which they are connected are shown next to the terminals). As such, to achieve right atrial sensing and pacing, the connector includes at least a right atrial tip terminal ($A_R$ TIP) 942 adapted for connection to the atrial tip electrode 822.

To achieve left atrial and ventricular sensing, pacing and shocking, the connector includes at least a left ventricular tip terminal ($V_L$ TIP) 944, a left atrial ring terminal ($A_L$ RING) 946, and a left atrial shocking terminal ($A_L$ COIL) 948, which are adapted for connection to the left ventricular ring electrode 826, the left atrial tip electrode 827, and the left atrial coil electrode 828, respectively.

To support right ventricle sensing, pacing and shocking, the connector further includes a right ventricular tip terminal ($V_R$ TIP) 952, a right ventricular ring terminal ($V_R$ RING) 954, a right ventricular shocking terminal ($R_V$ COIL) 956, and an SVC shocking terminal (SVC COIL) 958, which are adapted for connection to the right ventricular tip electrode 832, right ventricular ring electrode 834, the RV coil electrode 136, and the SVC coil electrode 138, respectively.

An atrial pulse generator 970 and a ventricular pulse generator 972 generate pacing stimulation pulses for delivery by the right atrial lead 820, the right ventricular lead 830, and/or the coronary sinus lead 824 via an electrode configuration switch 974. It is understood that in order to provide stimulation therapy in each of the four chambers of the heart, the atrial and ventricular pulse generators, 970 and 972, may include dedicated, independent pulse generators, multiplexed pulse generators, or shared pulse generators. The pulse generators, 970 and 972, are controlled by the microcontroller 960 via appropriate control signals, 976 and 978, respectively, to trigger or inhibit the stimulation pulses.

The microcontroller 960 further includes timing control circuitry 979 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 974 includes a plurality of switches for connecting the desired electrodes to the appropriate I/O circuits, thereby providing complete electrode programmability. Accordingly, the switch 974, in response to a control signal 980 from the microcontroller 960, determines the polarity of the stimulation pulses (e.g., unipolar, bipolar, etc.) by selectively closing the appropriate combination of switches (not shown) as is known in the art.

Atrial sensing circuits 982 and ventricular sensing circuits 984 may also be selectively coupled to the right atrial lead 820, coronary sinus lead 824, and the right ventricular lead 830, through the switch 974 for detecting the presence of cardiac activity in each of the four chambers of the heart. Accordingly, the atrial (ATR. SENSE) and ventricular (VTR. SENSE) sensing circuits, 982 and 984, may include dedicated sense amplifiers, multiplexed amplifiers, or shared amplifiers. The switch 974 determines the "sensing polarity" of the cardiac signal by selectively closing the appropriate switches, as is also known in the art. In this way, the clinician may program the sensing polarity independent of the stimulation polarity.

Each sensing circuit, 982 and 984, preferably employs one or more low power, precision amplifiers with programmable gain and/or automatic gain control, bandpass filtering, and a threshold detection circuit, as known in the art, to selectively sense the cardiac signal of interest. The automatic gain control enables the device 810 to deal effectively with the difficult problem of sensing the low amplitude signal characteristics of atrial or ventricular fibrillation. Such sensing circuits, 982 and 984, can be used to determine cardiac performance values used in the present invention. Alternatively, an automatic sensitivity control circuit may be used to effectively deal with signals of varying amplitude.

The outputs of the atrial and ventricular sensing circuits, 982 and 984, are connected to the microcontroller 960 which, in turn, are able to trigger or inhibit the atrial and ventricular pulse generators, 970 and 972, respectively, in a demand fashion in response to the absence or presence of cardiac activity, in the appropriate chambers of the heart. The sensing circuits, 982 and 984, in turn, receive control signals over signal lines, 986 and 988, from the microcontroller 960 for purposes of measuring cardiac performance at appropriate times, and for controlling the gain, threshold, polarization charge removal circuitry (not shown), and timing of any blocking circuitry (not shown) coupled to the inputs of the sensing circuits, 982 and 986.

For arrhythmia detection, the device 810 includes an arrhythmia detector 962 that utilizes the atrial and ventricular sensing circuits, 982 and 984, to sense cardiac signals to determine whether a rhythm is physiologic or pathologic. The timing intervals between sensed events (e.g., P-waves, R-waves, and depolarization signals associated with fibrillation) can be classified by the microcontroller 960 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 962 can perform arrhythmia discrimination, e.g., using measures of arterial blood pressure determined in accordance with embodiments of the present invention. Exemplary details of such arrhythmia discrimination, including tachyarrhythmia classification, are discussed above. The arrhythmia detector 962 can be implemented within the microcontroller 960, as shown in FIG. 9. Thus, this detector 962 can be implemented by software, firmware, or combinations thereof. It is also possible that all, or portions, of the arrhythmia detector 962 can be implemented using hardware. Further, it is also possible that all, or portions, of the arrhythmia detector 962 can be implemented separate from the microcontroller 960.

In accordance with embodiments of the present invention, the implantable device 810 includes an arterial blood pressure monitor 967, which can determine surrogates of SP, DP, MAP and/or PP, and changes in the same, using the techniques described above with reference to FIGS. 2-6. The arterial blood pressure monitor 967 can be implemented within the microcontroller 960, as shown in FIG. 9, and can the be implemented by software, firmware, or combinations thereof. It is also possible that all, or portions, of the monitor 967 to be implemented using hardware. Further, it is also possible that all, or portions, of the monitor 967 to be implemented separate from the microcontroller 960. The arterial blood pressure monitor 967 can be used in a closed loop control system to provide an assessment of hemodynamic stability during pacing parameter adjustments, and/or as an assessment of hemodynamic stability during a detected arrhythmia. Such measures of hemodynamic stability can be used when determining which anti-arrhythmia therapy options are appropriate.

In accordance with embodiments of the present invention, the implantable device 810 also includes a cardiac afterload monitor 964, which can monitor surrogates of CA, and changes in the same, using techniques described with reference to FIG. 7 and FIGS. 2A-2F. The CA monitor 964 can be implemented within the microcontroller 960, as shown in FIG. 9. Thus, this monitor 964 can be implemented by software, firmware, or combinations thereof. It is also possible that all, or portions, of the CA monitor 964 can be implemented using hardware. Further, it is also possible that all, or portions, of the ischemia detector 964 can be implemented separate from the microcontroller 960.

The implantable device 810 can also include a pacing controller 966, which can adjust a pacing rate and/or pacing intervals based on measures of arterial blood pressure, in accordance with embodiments of the present invention. The pacing controller 966 can be implemented within the microcontroller 960, as shown in FIG. 9. Thus, the pacing controller 966 can be implemented by software, firmware, or combinations thereof. It is also possible that all, or portions, of the pacing controller 966 can be implemented using hardware. Further, it is also possible that all, or portions, of the pacing controller 966 can be implemented separate from the microcontroller 960.

The implantable device can also include a medication pump 903, which can deliver medication to a patient if the patient's arterial blood pressure levels exceed or fall below specific thresholds. Information regarding implantable medication pumps may be found in U.S. Pat. No. 4,731,051 (Fischell) and in U.S. Pat. No. 4,947,845 (Davis), both of which are incorporated by reference herein.

Still referring to FIG. 9, cardiac signals are also applied to the inputs of an analog-to-digital (A/D) data acquisition system 990. The data acquisition system 990 is configured to acquire IEGM and/or ECG signals, convert the raw analog data into a digital signal, and store the digital signals for later processing and/or telemetric transmission to an external device 902. The data acquisition system 990 can be coupled to the right atrial lead 820, the coronary sinus lead 824, and the right ventricular lead 830 through the switch 974 to sample cardiac signals across any pair of desired electrodes. In specific embodiments, the data acquisition system 990 may be used to acquire IEGM signals for the analysis of changes in the ST-segment for detecting myocardial ischemia, and for monitoring arterial blood pressure using techniques described above.

The data acquisition system 990 can be coupled to the microcontroller 960, or other detection circuitry, for detecting an evoked response from the heart 812 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 960 detects a depolarization signal during a window following a stimulation pulse, the presence of which indicates that capture has occurred. The microcontroller 960 enables capture detection by triggering the ventricular pulse generator 972 to generate a stimulation pulse, starting a capture detection window using the timing control circuitry 979 within the microcontroller 960, and enabling the data acquisition system 990 via control signal 992 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention.

The microcontroller 960 is further coupled to the memory 994 by a suitable data/address bus 996, wherein the programmable operating parameters used by the microcontroller 960 are stored and modified, as required, in order to customize the operation of the implantable device 810 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 812 within each respective tier of therapy. The memory 994 can also store data about surrogates of DP, SP, MAP, PP and/or CA.

The operating parameters of the implantable device 810 may be non-invasively programmed into the memory 994 through a telemetry circuit 901 in telemetric communication with an external device 902, such as a programmer, transtelephonic transceiver, or a diagnostic system analyzer. The telemetry circuit 901 can be activated by the microcontroller 960 by a control signal 906. The telemetry circuit 901 advantageously allows intracardiac electrograms and status information relating to the operation of the device 810 (as contained in the microcontroller 960 or memory 994) to be sent to the external device 902 through an established communication link 904. The telemetry circuit can also be use to transmit arterial blood pressure data to the external device 902.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 810 additionally includes a battery 911 which provides operating power to all of the circuits shown in FIG. 9. If the implantable device 810 also employs shocking therapy, the battery 911 should be capable of operating at low current drains for long periods of time, and then be capable of providing high-current pulses (for capacitor charging) when the patient requires a shock pulse. The battery 911 should also have a predictable discharge characteristic so that elective replacement time can be detected.

The implantable device 810 can also include a magnet detection circuitry (not shown), coupled to the microcontroller 960. It is the purpose of the magnet detection circuitry to detect when a magnet is placed over the implantable device 810, which magnet may be used by a clinician to perform various test functions of the implantable device 810 and/or to signal the microcontroller 960 that the external programmer 902 is in place to receive or transmit data to the microcontroller 960 through the telemetry circuits 901.

As further shown in FIG. 9, the device 810 is also shown as having an impedance measuring circuit 913 which is enabled by the microcontroller 960 via a control signal 914. The known uses for an impedance measuring circuit 913 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 913 is advantageously coupled to the switch 974 so that any desired electrode may be used. The impedance measuring circuit 913 is not critical to the present invention and is shown only for completeness.

In the case where the implantable device 810 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 960 further controls a shocking circuit 916 by way of a control signal 918. The shocking circuit 916 generates shocking pulses of low (up to 0.5 Joules), moderate (0.5-10 Joules), or high energy (11 to 40 Joules), as controlled by the microcontroller 960. Such shocking pulses are applied to the patient's heart 812 through at least two shocking electrodes, and as shown in this embodiment, selected from the left atrial coil electrode 828, the RV coil electrode 836, and/or the SVC coil electrode 838. As noted above, the housing 840 may act as an active electrode in combination with the RV electrode 836, or as part of a split electrical vector using the SVC coil electrode 838 or the left atrial coil electrode 828 (i.e., using the RV electrode as a common electrode).

The above described implantable device 810 was described as an exemplary pacing device. One or ordinary skill in the art would understand that embodiments of the present invention can be used with alternative types of implantable devices. Accordingly, embodiments of the present invention should not be limited to use only with the above described device.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in the flow diagrams. Further, it may be possible to change the order of some of the steps shown in flow diagrams, without substantially changing the overall events and results. For another example, it is possible to change the boundaries of some of the blocks shown in FIG. 9.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use in an implantable system including an implantable photoplethysmography (PPG) sensor, a method for determining a surrogate of cardiac afterload (CA) in a subject, comprising:
   (a) obtaining an arterial PPG waveform measurement using the implantable PPG sensor implanted in the subject;
   (b) determining a metric of a terminal portion of the arterial photoplethysmography (PPG) waveform, wherein the terminal portion is from a maximum of the arterial PPG waveform to the following minimum of the PPG waveform; and
   (c) determining the surrogate of CA in the subject as a function of the metric of the terminal portion of the arterial PPG waveform in step b) based on the measured arterial PPG waveform by the implanted PPG sensor.

2. The method of claim 1, wherein the arterial PPG waveform comprises an averaged arterial PPG waveform that is produced by averaging a plurality of cardiac cycles of a PPG signal obtained from the implanted PPG sensor.

3. The method of claim 1, further comprising:
   repeating steps (a) and (b) and (c) from time to time; and
   monitoring changes in CA by monitoring changes in the surrogate of CA as steps (a) and (b) and (c) are repeated from time to time.

4. The method of claim 1, wherein, the metric of the terminal portion comprises at least one of the following:
   an integral from a maximum to the following minimum of the arterial PPG waveform;
   an integral from a dicrotic notch to the following minimum of the PPG waveform;
   a terminal deceleration slope (TDS), which is a downward slope from a maximum to the following minimum of the arterial PPG waveform;
   a beginning terminal deceleration slope (BTDS), which is a downward slope from a maximum to the following dicrotic notch of the arterial PPG waveform;
   a total relaxation time (TRT), which is a time from a maximum to the following minimum of the atrial PPG signal; and
   a terminal deceleration time (TeDT), which is a time from a dicrotic notch to the following minimum of the atrial PPG signal.

* * * * *